US008377082B2

(12) United States Patent
Clague et al.

(10) Patent No.: US 8,377,082 B2
(45) Date of Patent: Feb. 19, 2013

(54) METHODS AND APPARATUS FOR MAKING PRECISE INCISIONS IN BODY VESSELS

(75) Inventors: Cynthia T. Clague, Minnetonka, MN (US); Scott E. Jahns, Hudson, WI (US); Paul T. Rothstein, Maple Grove, MN (US); Thomas P. Daigle, Corcoran, MN (US); Raymond W. Usher, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 2937 days.

(21) Appl. No.: 10/694,037

(22) Filed: Oct. 27, 2003

(65) Prior Publication Data

US 2004/0138685 A1 Jul. 15, 2004

Related U.S. Application Data

(60) Provisional application No. 60/439,828, filed on Jan. 14, 2003.

(51) Int. Cl.
*A61B 17/22* (2006.01)
*A61B 17/32* (2006.01)

(52) U.S. Cl. ........................................ 606/159; 606/174

(58) Field of Classification Search .................. 606/185, 606/159, 169, 174
See application file for complete search history.

(56) References Cited

U.S. PATENT DOCUMENTS

| 3,166,072 A | 1/1965 | Sullivan |
| 4,216,776 A | 8/1980 | Downie et al. |
| 4,366,819 A | 1/1983 | Kasier |
| 5,129,913 A | 7/1992 | Ruppert |
| 5,192,294 A | 3/1993 | Blake, III |
| 5,314,440 A * | 5/1994 | Shapiro ............... 359/676 |
| 5,385,606 A | 1/1995 | Kowanko ............. 106/124 |
| 5,452,733 A | 9/1995 | Sterman et al. ........... 128/898 |
| 5,464,447 A | 11/1995 | Fogarty et al. .......... 607/129 |
| 5,584,848 A | 12/1996 | Yoon |
| 5,586,792 A | 12/1996 | Kalahasthy et al. |
| 5,588,949 A | 12/1996 | Taylor et al. |
| 5,676,670 A | 10/1997 | Kim |
| 5,690,662 A | 11/1997 | Chiu et al. |
| 5,695,504 A | 12/1997 | Gifford, III et al. ........ 606/153 |
| 5,707,380 A | 1/1998 | Hinchiffe et al. ........... 606/153 |
| 5,716,392 A | 2/1998 | Bourgeois et al. ........... 607/132 |
| 5,776,154 A | 7/1998 | Taylor et al. ............... 606/167 |
| 5,799,661 A | 9/1998 | Boyd et al. ............... 128/898 |
| 5,817,113 A | 10/1998 | Gifford, III et al. |
| 5,830,224 A | 11/1998 | Cohn et al. ............... 606/167 |
| 5,868,770 A | 2/1999 | Rygaard .................. 606/167 |
| 5,875,782 A | 3/1999 | Ferrari et al. ............... 128/898 |

(Continued)

FOREIGN PATENT DOCUMENTS

| EP | 1330986 A1 | 7/2003 |
| JP | 2003-210473 * | 7/2003 |

(Continued)

*Primary Examiner* — Tuan V Nguyen

(57) ABSTRACT

Methods and apparatus employed in surgery involving making precise incisions through body vessel walls, particularly coronary arteries. A body vessel cutting instrument comprises an elongated instrument shaft extending between a shaft proximal end adapted to be manipulated outside the patient's body and a shaft distal end and having a shaft axis and first and second cutting blades supported at the shaft distal end. The first cutting blade extends substantially orthogonally or laterally to the shaft axis and has a first cutting edge extending along a trailing side, a cutting tip at the first cutting blade free end, and an atraumatic blunt surface along the leading side. The second cutting blade has a second cutting edge extending along a leading side, whereby the first and second cutting edges face one another and are brought together to slit a vessel wall.

17 Claims, 20 Drawing Sheets

U.S. PATENT DOCUMENTS

| | | | |
|---|---|---|---|
| 5,893,369 A | 4/1999 | LeMole | |
| 5,893,865 A | 4/1999 | Swindle et al. | |
| 5,904,679 A | 5/1999 | Clayman | 606/39 |
| 5,910,153 A | 6/1999 | Mayenberger | |
| 5,972,017 A | 10/1999 | Berg et al. | 606/198 |
| 5,976,069 A * | 11/1999 | Navia et al. | 600/37 |
| 5,976,178 A | 11/1999 | Goldsteen et al. | 623/1 |
| 6,022,367 A | 2/2000 | Sherts | |
| 6,026,814 A | 2/2000 | LaFontaine et al. | 128/898 |
| 6,036,641 A * | 3/2000 | Taylor et al. | 600/231 |
| 6,036,710 A | 3/2000 | McGarry et al. | |
| 6,068,637 A | 5/2000 | Popov et al. | 606/159 |
| 6,071,295 A | 6/2000 | Takahashi | 606/191 |
| 6,080,175 A | 6/2000 | Hogendijk | 606/185 |
| 6,099,542 A | 8/2000 | Cohn et al. | 606/167 |
| 6,110,188 A | 8/2000 | Narcisco, Jr. | |
| 6,120,436 A | 9/2000 | Anderson et al. | 600/201 |
| 6,162,236 A | 12/2000 | Osada | |
| 6,231,565 B1 | 5/2001 | Tovey et al. | 606/1 |
| 6,248,117 B1 | 6/2001 | Blatter | 606/153 |
| 6,270,516 B1 | 8/2001 | Tanner et al. | 606/213 |
| 6,331,158 B1 * | 12/2001 | Hu et al. | 600/232 |
| 6,332,468 B1 | 12/2001 | Benetti | 128/898 |
| 6,371,964 B1 | 4/2002 | Vargas et al. | 606/153 |
| 6,387,105 B1 | 5/2002 | Gifford, III et al. | |
| 6,387,108 B1 * | 5/2002 | Taylor et al. | 606/167 |
| 6,394,948 B1 | 5/2002 | Borst et al. | 600/37 |
| 6,416,527 B1 | 7/2002 | Berg et al. | |
| 6,517,558 B2 | 2/2003 | Gittings et al. | |
| 6,635,214 B2 | 10/2003 | Rapacki et al. | |
| 6,651,670 B2 | 11/2003 | Rapacki et al. | |
| 6,719,768 B1 | 4/2004 | Cole et al. | |
| 6,730,103 B2 | 5/2004 | Dakov | |
| 6,802,847 B1 | 10/2004 | Carson et al. | |
| 6,808,498 B2 | 10/2004 | Laroya et al. | |
| 6,896,687 B2 | 5/2005 | Dakov | |
| 2002/0022857 A1 | 2/2002 | Goldsteen et al. | |
| 2003/0144679 A1 | 7/2003 | Irisawa | |
| 2003/0199923 A1 | 10/2003 | Khairkhahan et al. | |
| 2003/0199986 A1 | 10/2003 | McWeeney et al. | |

FOREIGN PATENT DOCUMENTS

| | | |
|---|---|---|
| WO | WO 02/28287 | 4/2002 |

* cited by examiner

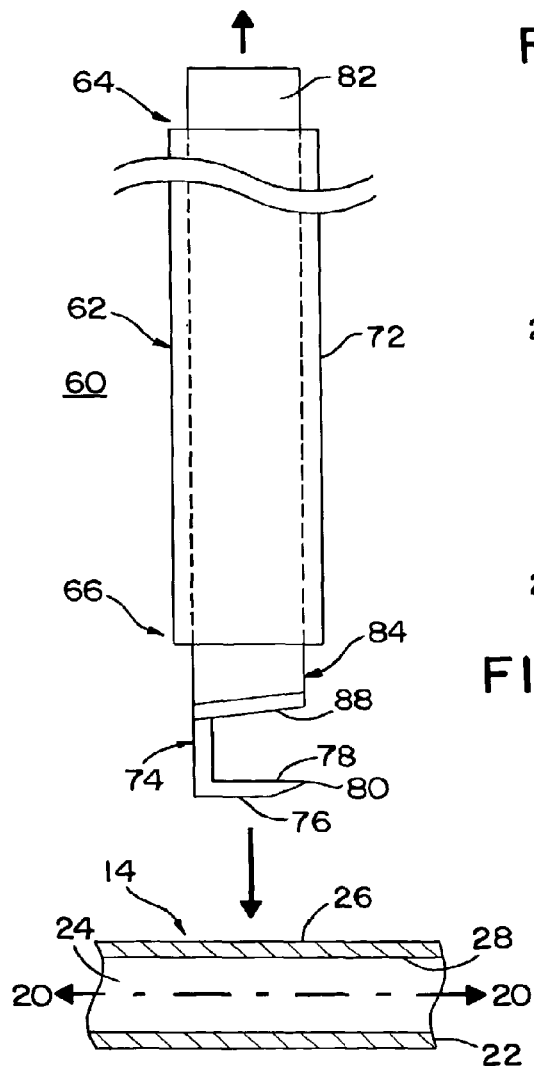
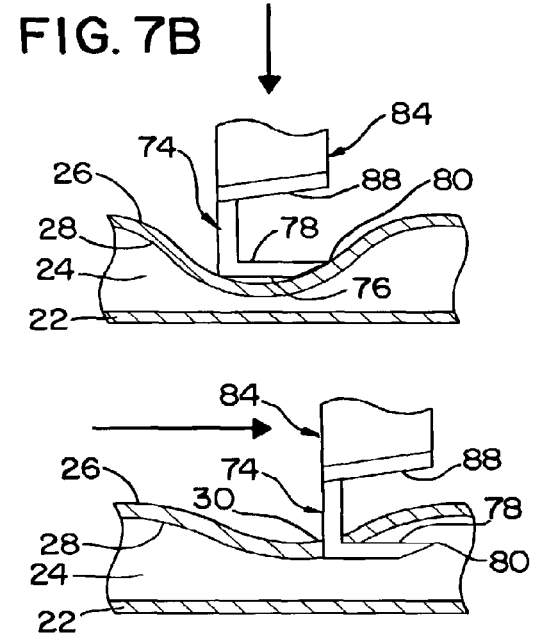
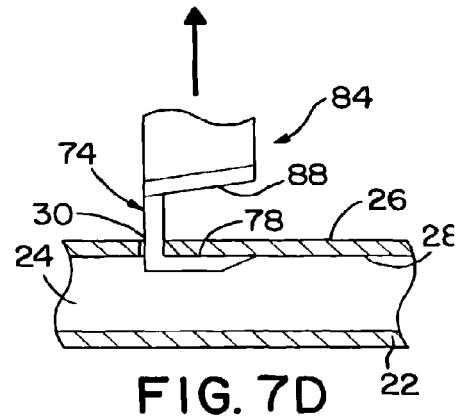
FIG. 7A
FIG. 7B
FIG. 7C
FIG. 7D

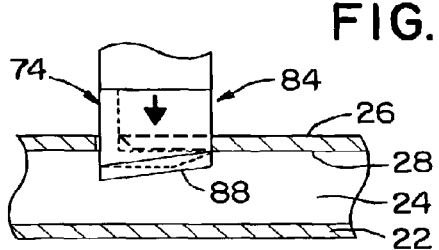
FIG. 7E
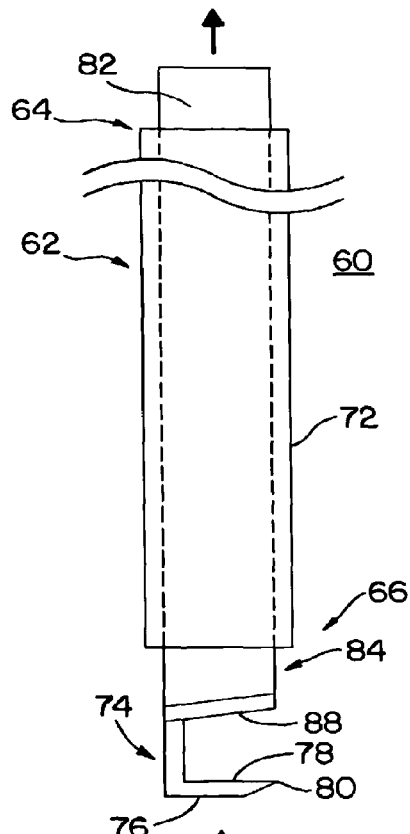
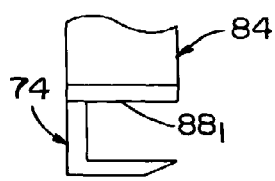 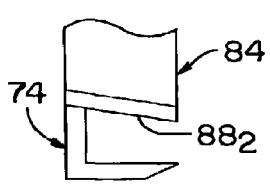
FIG. 8A   FIG. 8B
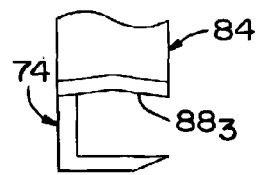 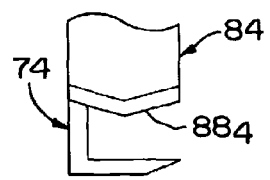
FIG. 8C   FIG. 8D
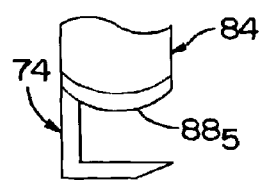  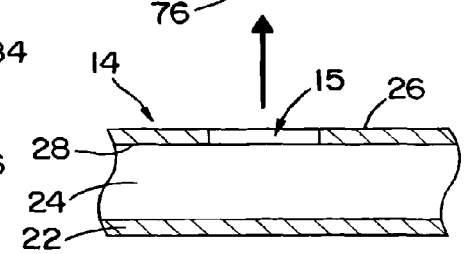
FIG. 8E   FIG. 8F   FIG. 7F

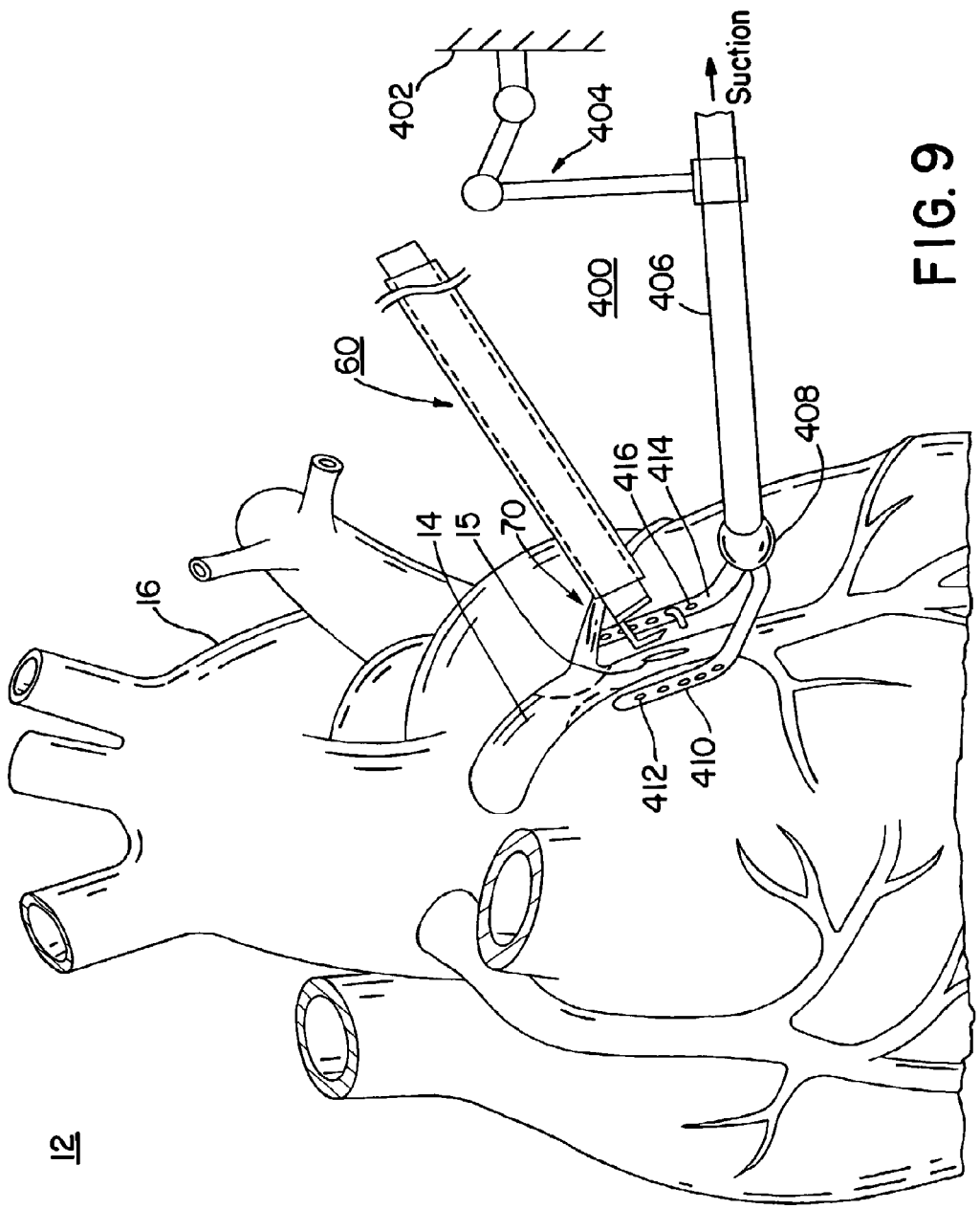

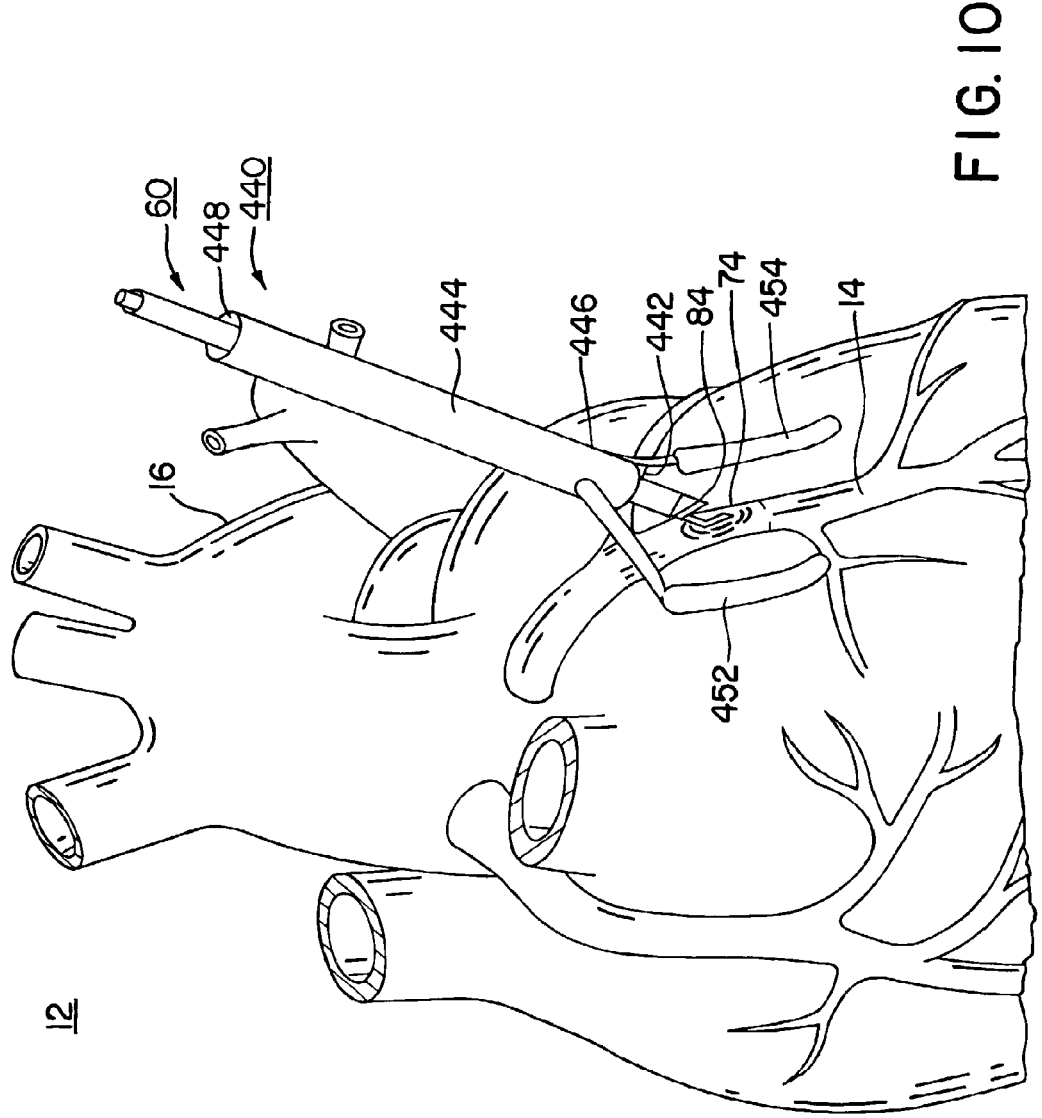

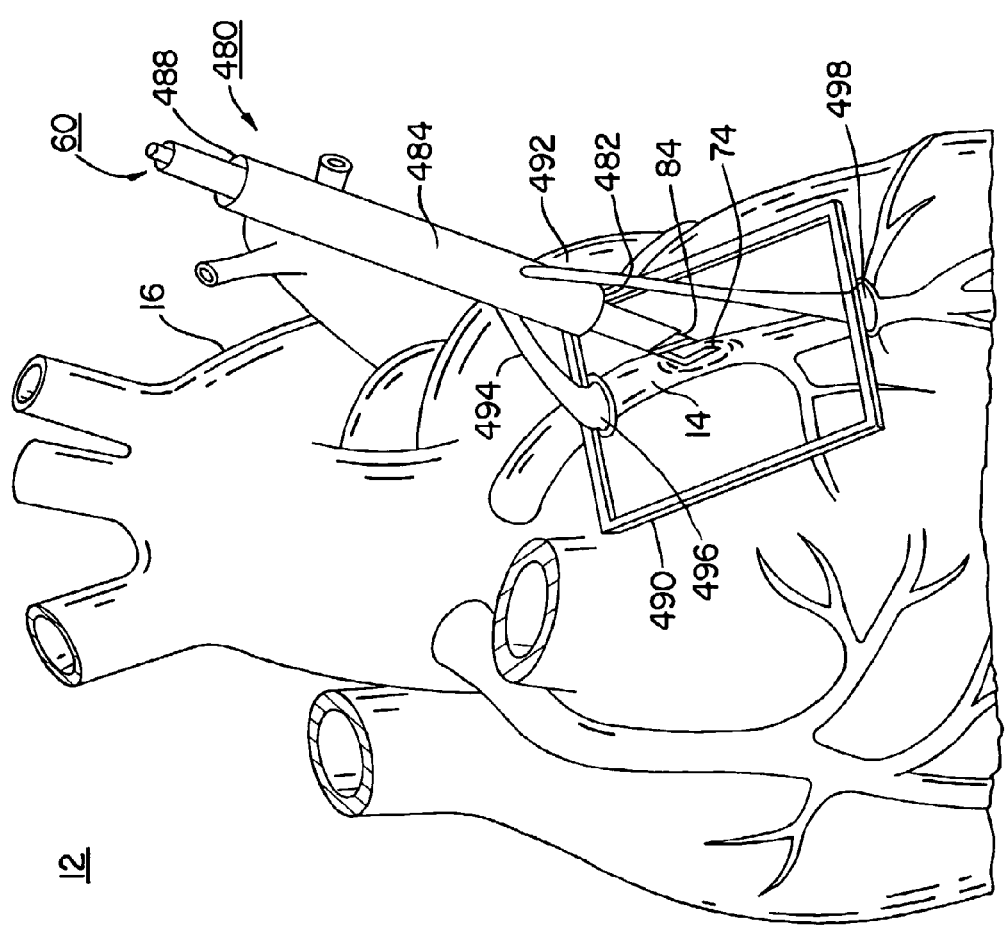

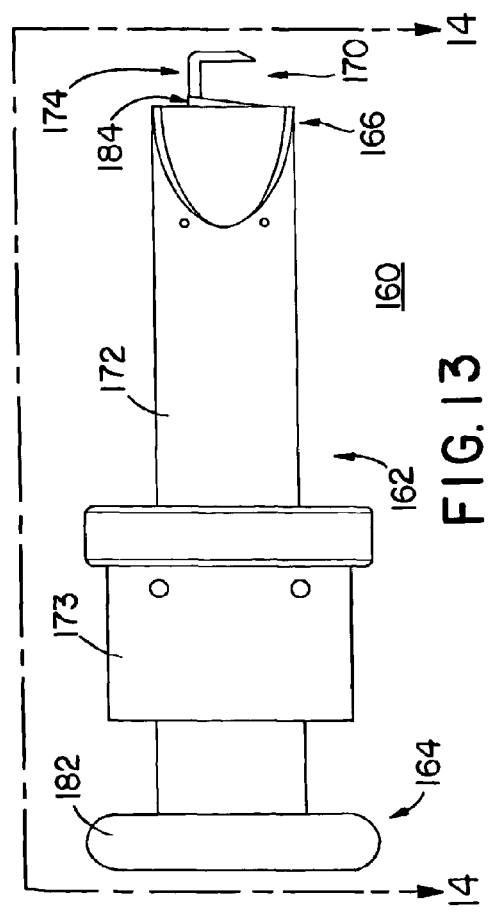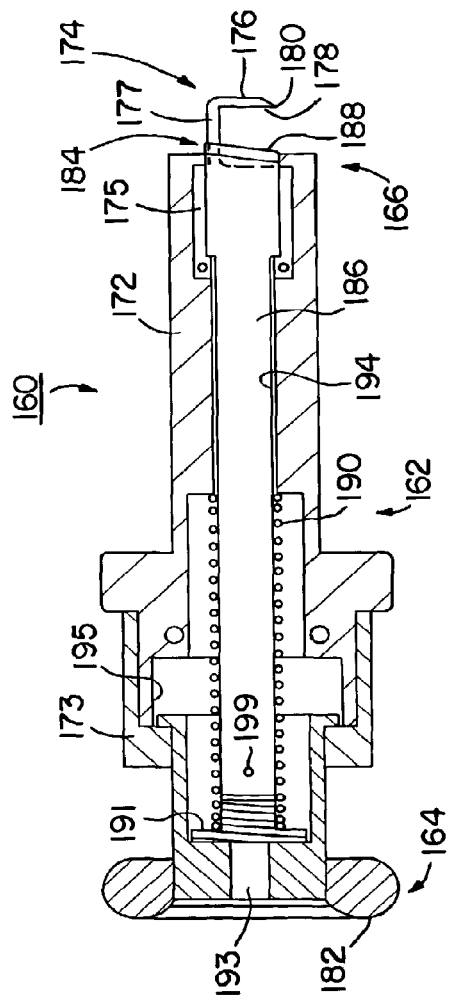

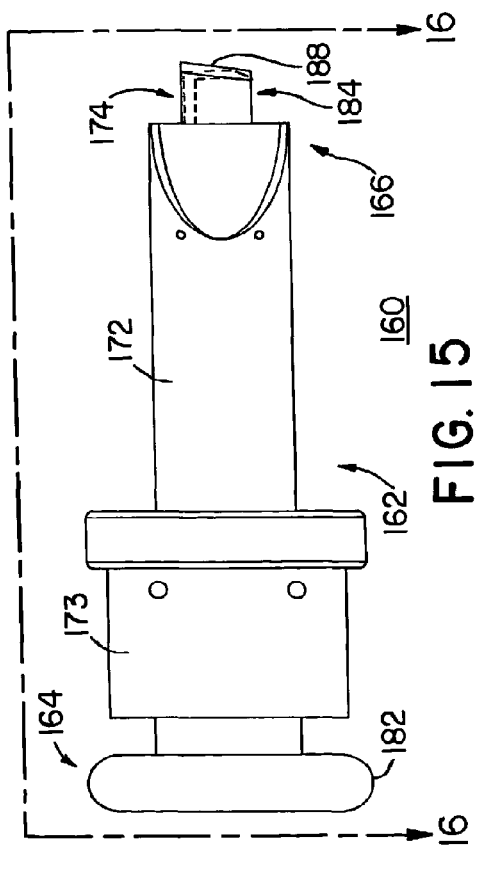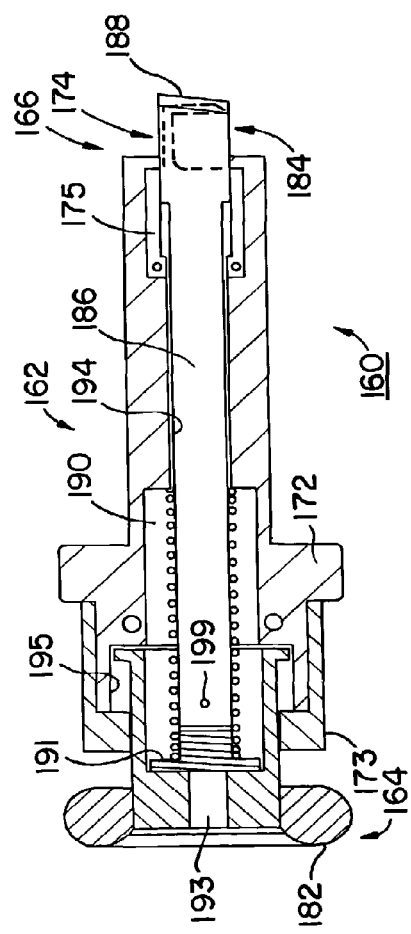

METHODS AND APPARATUS FOR MAKING PRECISE INCISIONS IN BODY VESSELS

This application claims benefit of Provisional No. 60/439,828 filed Jan. 14, 2003.

REFERENCE TO RELATED APPLICATION

Reference is made to commonly assigned U.S. patent application Ser. No. 10/278,966 filed Oct. 23, 2002 for ELECTROSURGICAL METHODS AND APPARATUS FOR MAKING PRECISE INCISIONS IN BODY VESSELS in the names of Cynthia T. Clague et al.

FIELD OF THE INVENTION

The present invention pertains to methods and apparatus employed in surgery involving making precise incisions in vessels of the body, particularly cardiac blood vessels in coronary revascularization procedures conducted on the stopped or beating heart.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is caused by atherosclerosis, a form of arteriosclerosis.

Atherosclerosis is a disease in which the lumen (interior passage) of an artery becomes stenosed (narrowed) or even totally occluded (blocked) by an accumulation of fibrous, fatty, or calcified tissue. Over time this tissue, known in medicine as an atheroma, hardens and occludes the artery. The partial stenosis or full occlusion of the coronary arteries that supply the heart muscle leads to ischemia (deficient blood flow) of the heart muscle, angina (chest pain), and can lead to infarction (heart attack) or patient death. Although drug therapies and modifications to diet and lifestyle show great promise for preventing and treating atherosclerotic vascular disease, many patients urgently require restoration of blood flow that has already been lost, especially in those having severely or totally occluded blood vessels.

In many cases, a patient suffering a coronary vessel obstruction or restriction undergoes a coronary artery bypass graft (CABG) surgical procedure, more commonly known as a "heart bypass" operation to restore normal oxygenated blood flow to the heart muscle downstream of the obstruction or restriction. More particularly, a fluid connection or "distal anastomosis." is surgically established between a source vessel of oxygenated blood and the obstructed or restricted target coronary artery downstream or distal to the obstruction or restriction to restore the flow of oxygenated blood to the heart muscle. In one approach, the surgeon attaches an available source vessel, e.g., an internal mammary artery (IMA), directly to the obstructed target coronary artery at the distal anastomosis site downstream from the obstruction or restriction.

There are a number of alternative approaches to CABG surgery. In one approach, the surgeon harvests a graft blood vessel from the patient's venous system and prepares its proximal and distal ends to be attached in a "proximal anastomosis" and a "distal anastomosis" bypassing the occlusion. This type of graft is commonly known as a "free" graft. The proximal anastomosis can be located proximal or upstream to the occlusion or to another vessel supplying oxygenated blood, e.g., the aorta. Typically, a section of the saphenous vein is harvested from the patient's body. Sometimes, the internal mammary artery (IMA) is used as the graft blood vessel or the radial artery is used as arterial conduit and the proximal anastomosis has to be made. In another approach, artery-to-artery bypass procedures have been utilized in which an arterial source of oxygenated blood, e.g., the left IMA or right IMA, is severed and a portion is dissected away from supporting tissue so that the severed end can be anastomosed to the obstructed coronary artery distally to the stenosis or occlusion. More recently, other arteries have been used in such procedures, including the inferior epigastric arteries and gastroepiploic arteries. It is also stated in U.S. Pat. No. 6,080,175 that a conventional electrosurgical instrument can be introduced through a port or incision and used to dissect and prepare the bypass graft vessel for coronary anastomosis while viewing the procedure through a thoracoscope.

It is necessary to access and prepare the site or sites of the vessel wall of the target coronary artery where the proximal and/or distal anastomosis is to be completed and to then make the surgical attachments of the blood vessels. First, it is necessary to isolate the anastomosis site of the target coronary artery from the epicardial tissues and overlying fatty layers. Typically, blunt, rounded #15 scalpel blades are employed to dissect these tissues and layers away from the target coronary artery.

Generally, blood flow in the target coronary artery is interrupted by, for example, temporary ligation or clamping of the artery proximal and distal of the anastomosis site, and the target coronary arterial wall is opened to form an arteriotomy, that is, an elongated incision at the anastomosis site extending parallel to the axis of the coronary vessel and equally spaced from the sides of the coronary artery that are still embedded in or against the epicardium. The arteriotomy is typically created by use of a very sharp, pointed, #11 scalpel blade to perforate the coronary arterial wall, and the puncture is elongated the requisite length using scissors. A "perfect arteriotomy" is an incision that has straight edges, that does not stray from the axial alignment and equal distance from the sides of the coronary artery, and is of the requisite length.

Similarly, it is necessary to prepare the attachment end of the source vessel by cutting the source vessel end at an appropriate angle for an end-to-side or end-to-end anastomosis or by forming an elongated arteriotomy in the source vessel wall of a suitable length that is axially aligned with the source vessel axis for a side-to-side anastomosis. Typically, the surgeon uses surgical scalpels and scissors to shape the source vessel end or make the elongated arteriotomy slit in the source vessel, and uses sutures or clips to close the open severed end.

In the example depicted schematically in FIG. 1, the heart 12 is prepared as described above for an end-to-side anastomosis of the surgically freed, severed, and appropriately shaped vessel end 31 of the left IMA 42 branching from the aorta 16 and left subclavian artery 18 to the prepared arteriotomy 15 in the vessel wall of the left anterior descending (LAD) coronary artery 14 downstream from the obstruction 38. Similarly, in the example depicted schematically in FIG. 3, the heart 12 is prepared as described above for a side-to-side anastomosis of the left IMA 42 to the prepared arteriotomy 15 in the vessel wall of the LAD coronary artery 14. In the side-to-side anastomosis, an arteriotomy 33 is made in the freed segment of the left IMA 30, and the vessel end 31 is sutured closed.

The prepared end or elongated arteriotomy of the bypass graft or source vessel is attached or anastomosed to the target coronary artery at the arteriotomy in a manner that prevents leakage of blood employing sutures, staples, surgical adhesives and/or various artificial anastomosis devices. For example, an end-to-side anastomosis 35 of the shaped vessel end 31 of the left IMA 42 to the prepared arteriotomy 15 in the vessel wall of the LAD coronary artery 14 is illustrated in FIG. 2. And a side-to-side anastomosis 37 joining the arteriotomy 33 of the left IMA 42 to the prepared arteriotomy 15 of the LAD coronary artery 14 is illustrated, for example, in FIG. 4.

The inner, endothelial layer, vessel linings are less thrombogenic than the outer epithelial layers of blood vessels. So, in one approach, the attachment is made by everting and applying the interior linings of the bypass graft or source vessel and the target coronary artery against one another and suturing or gluing or otherwise attaching the interior linings together. Various types of artificial biocompatible reinforcement sleeves or rings, e.g., those shown in the above-referenced '369 patent can also be used in the anastomosis. Currently, a number of mechanical anastomotic devices, materials, techniques, and procedures are being developed for facilitating the process of forming an anastomosis including vascular clips or staplers, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques can include the use of various biomaterials and/or biocompatible agents. See, for example, U.S. Pat. Nos. 5,385,606, 5,695,504, 5,707,380, 5,972,017 and 5,976,178, and 6,231,565.

Various examples of forming the target vessel arteriotomy or arteriotomies, the shaped end or side wall arteriotomy of the source vessel, and the positioning and attachment of the source vessel and target artery together are set forth in U.S. Pat. Nos. 5,799,661, 5,868,770, 5,893,369, 6,026,814, 6,071,295, 6,080,175, 6,248,117, 6,331,158, and 6,332,468.

In a conventional bypass graft or CABG procedure, the surgeon exposes the obstructed coronary vessel through an open chest surgical exposure or thoracotomy providing direct visualization and access to the epicardium. Typically, fat layers that make it difficult to see either the artery or the occlusion cover the epicardial surface and the obstructed cardiac artery. However, surgeons are able to dissect the fat away to expose the artery and manually palpate the heart to feel the relatively stiff or rigid occlusion within the artery as a result of their training and experience. The surgeon can determine the location and length of the occlusion as well as suitable sites of the target coronary artery for the proximal and distal anastomoses with some degree of success.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced in order to reduce the risk of morbidity, expense, trauma, patient mortality, infection, and other complications associated with open chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing CABG procedures performed while the heart is still beating using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through sleeves or ports inserted in the incisions, and a thoracoscope to view the accessed cardiac site while the procedure is performed as shown, for example, in the above-referenced '175, '295, '468 and '661 patents and in U.S. Pat. Nos. 5,464,447, and 5,716,392. Surgical trocars having a diameter of about 3 mm to 15 mm are filted into lumens of tubular trocar sleeves or ports, and the assemblies are inserted into skin incisions. The trocar tip is advanced to puncture the abdomen or chest to reach the pericardium, and the trocar is then withdrawn leaving the port in place. Surgical instruments and other devices such as fiber optic thoracoscopes can be inserted into the body cavity through the port lumens. As stated in the '468 patent, instruments advanced through trocars can include electrosurgical tools, graspers, forceps, scalpels, electrocautery devices, clip appliers, scissors, etc.

In the above-described procedures, the surgeon can stop the heart by utilizing a series of internal catheters to stop blood flow through the aorta and to administer cardioplegia solution. The endoscopic approach utilizes groin cannulation to establish cardiopulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures eliminate the need for any form of CPB, the extensive surgical procedures necessary to connect the patient to a CPB machine, and to stop the heart. A number of surgical instruments have been developed that attempt to stabilize or immobilize a portion of the beating heart that supports the target coronary artery and the anastomosis site. These beating heart procedures described, for example, in the above-referenced '158, '175, '770, '782, and '295 patents and in U.S. Pat. Nos. 5,976,069, and 6,120,436, can be performed on a heart exposed in a full or limited thoracotomy or accessed percutaneously.

For example, a retractor assembly disclosed in the above-referenced '158 patent mounts to and maintains the chest opening while supporting a stabilizer assembly that extends parallel stabilizer bars against the epicardium alongside the target coronary artery so that force is applied across the anastomosis site to suppress heart motion. The surgeon employs conventional manually applied clamps to block blood flow through the arterial lumen and scalpels and scissors to make the elongated incision of the arteriotomy.

Instruments are disclosed in the above-referenced '295 patent that apply suction to the epicardial surface around or alongside the anastomosis site to suppress heart motion.

Again, the surgeon employs the conventional manually applied clamps to block blood flow through the arterial lumen and a scalpel to make the elongated incision of the arteriotomy.

Instruments that combine the application of suction to the epicardial surface around or alongside the anastomosis site to suppress heart motion with a cutting mechanism for making the arteriotomy are disclosed in the above-referenced '175 and '770 patents. The surgical cutting instruments disclosed in the '770 and '175 patents include an elongated shaft having a proximal end, a distal end adapted for percutaneous insertion against the target coronary artery over the anastomosis site, and an axial lumen therebetween. A suction pad is formed at the distal end of the shaft, and a cutting element disposed within the lumen of the shaft near the distal end. A vacuum line is fluidly coupled to the lumen of the shaft and is adapted to connect to a vacuum source to provide a suction force at the distal end of the shaft. A control mechanism is provided to selectively block flow between the vacuum source and the lumen. The control mechanism may include a slide valve, an on/off button, or other equivalent mechanism for selectively closing and opening the vacuum pathway. A gripper assembly configured to grip a portion of the coronary artery is also disclosed in the '175 patent.

The cutting element and the shaft are relatively moveable between a retracted position and a cutting position. The cutting element is adapted to make the elongated slit of the arteriotomy in alignment with the axis of the coronary artery when the cutting element and the shaft are in the cutting position and the vacuum holds the anastomosis site steady.

The distal end of the shaft disclosed in the '175 patent has an outside diameter of less than about 5 mm, and the cutting element comprises at least one cutting element having a substantially straight blade cutting edge. The cutting edge is displaced at an angle of between about 15 to 30 degrees relative to a vertical axis through the cutting element. In one embodiment, the cutting element is fixed to an actuator push rod located within the lumen of the shaft, and connected to an actuator, preferably an actuator button, at a proximal end thereof. In another embodiment, the shaft is slidably mounted to a handle of the cutting instrument. An anchor, preferably a rigid rod coaxially disposed within the shaft, fixes the cutting element to the handle. An actuator member mounted to the shaft and biased by a spring is actuated to slide the shaft between retracted and cutting positions with respect to the cutting element.

Additionally or alternatively, at least one electrode may be disposed near the distal end of the shaft to effect or enhance cutting. The electrode may be operatively coupled to the cutting element, preferably substantially co-linearly coupled to the cutting edge. In the depicted embodiments, the electrode extends to the cutting tip of the cutting element opposite to the cutting blade. In use, the end of the electrode at the tip of the cutting element is placed against the coronary artery and energized by radio frequency energy as the cutting element is moved to the cutting position to facilitate making a small point incision or pilot hole in the coronary artery. Then, the cutting blade is fully advanced to make the elongated cut. Ultrasonic energy may be applied to the cutting element to effect or enhance cutting by the ultrasonically vibrating the cutting blade.

All of the above-described approaches employ a cutting blade to make the elongated slit of the arteriotomy. In most cases, the shaft must be carefully moved to advance the cutting blade along the length of the vessel wall without inadvertently pushing the tip of blade across the vessel lumen and through the vessel wall opposite to the intended slit. Damage can be caused to the vessel wall or the heart wall may be perforated if care is not taken.

In a further U.S. Pat. No. 5,776,154, hand-held instruments are disclosed for making arteriotomies in a cardiac artery of the beating heart accessed through a surgical incision through the chest wall. In one embodiment a fixed curved blade extends from the distal end of an elongated shaft having a handle at the shaft proximal end. The fixed curved blade takes the appearance of a scythe having a blunt leading or distal side, a cutting edge formed on the trailing or proximal side, and a point at the blade free end. In use, the shaft is extended through the incision to dispose the fixed curved blade adjacent the artery. The handle is manipulated to orient the shaft at an angle to the arterial wall enabling application of the point against the exterior surface of the arterial wall, and the point is pushed through the arterial wall. The shaft is straightened as the curved blade is inserted fully into the artery aligned with the axis of the artery. The blunt leading edge of the curved blade does not injure the arterial wall if it is pressed against the arterial wall. The shaft is again angled to apply the point against the interior surface of the arterial wall, and the shaft is pulled away from the arterial wall so that the cutting edge cuts through the arterial wall to form the elongated slit of the arteriotomy. The point may have several alternate shapes to facilitate penetration of the vessel wall while minimizing trauma to the surrounding tissue.

In a further embodiment of the above-referenced '154 patent, the shaft is formed of a movable shaft member supporting a cutting blade at its distal end and a fixed shaft member supporting a curved blade stop similar to the cutting blade of the first embodiment at its fixed end. The movable shaft member is movable from a position displaced from the blade stop to a position in engagement with the blade stop. The curved blade stop has a blunt leading or distal side, a trailing or proximal side, and a point at the stop free end. The cutting edge of the movable cutting blade is formed along the leading or distal side of the cutting blade. In use, the cutting blade is moved away from the blade stop, and the blade stop is inserted into the arterial lumen by manipulating the shaft in the same manner as the first embodiment to dispose the blade stop within the arterial lumen and aligned with the arterial axis. The movable shaft member is then advanced distally along the length of the fixed shaft member until the movable cutting blade cutting edge cuts through the arterial wall and engages the blade stop.

The use of these embodiments requires a relatively larger incision than afforded by a percutaneous access so that the shaft can be angled back and forth at the handle to insert the tip of the curved blade or blade stop through the arterial wall into the artery lumen and then back through the arterial wall to position it to cut or enable cutting of an arteriotomy through the arterial wall.

Moreover, achievement of consistent, precise slit lengths is made difficult when inserting the tip of the curved blade or blade stop disclosed in the '154 patent through the arterial wall into the lumen and then back out through the vessel wall in a manner similar to using a curved sewing needle. The slit length is dependent on the depth ("bite of tissue") that the tip is inserted into the vessel lumen before the cutting blade or stop is turned back to point the tip outward to penetrate back through the arterial wall. The distance along the artery from the insertion point to the exit point is dependent on how deep the tip is inserted into the arterial lumen and how quickly it is turned to position it at the exit point. The depth of insertion of the tip is dependent upon the arterial lumen diameter. For example, it would be difficult to achieve a 4 mm long slit if the artery lumen is about 1.5 mm in diameter. Consequently, the slit that is made may be too short if the insertion depth is shallow, requiring extending the slit by repeating the procedure or using another instrument In addition, it may be necessary to probe the sharp tip about the inner surface of the arterial wall to position the tip to be brought back through the arterial wall, possibly causing damage to the endothelial layer.

A vessel wall cutting tool or instrument is needed for making an arteriotomy or a similar slit in a vessel wall that avoids or minimizes the need to move the cutting instrument or the cutting blade along the vessel wall to slit the vessel wall to a desired length and that can be manipulated while inserted through a relatively small incision afforded by a percutaneous port or limited thoracotomy to perforate the vessel wall.

Such a vessel wall cutting tool or instrument should be usable with or incorporate stabilization of a section or area of the beating heart in the vicinity on encompassing an artery to facilitate forming an arteriotomy.

Such a vessel wall cutting tool or instrument should be usable with or incorporate a mechanism for occluding an artery or other blood vessel to inhibit blood loss through the incision as the incision is being made through the vessel wall.

SUMMARY OF THE INVENTION

The present invention is preferably embodied in a vessel wall cutting tool or instrument and methods for making precise elongated incisions or slits extending lengthwise along and through a body vessel wall, e.g., arteriotomy incisions or slits in coronary arteries and source vessels while the heart is beating, wherein ancillary damage to the vessel wall is minimized, and the cutting instrument can be employed through a relatively small incision afforded by a percutaneous port or limited thoracotomy.

The vessel wall cutting instrument of the present invention adapted to be inserted through an incision for making an elongated slit through a vessel wall and into a lumen of a body vessel of a patient comprises an elongated instrument shaft extending between a shaft proximal end adapted to be manipulated outside the patient's body and a shaft distal end and having a shaft axis. The vessel wall cutting instrument has first and second cutting blades supported at the shaft distal end. The first cutting blade is supported to extend substantially orthogonally or laterally to the shaft axis and has a first cutting edge extending along a trailing side of the first cutting blade, a cutting tip at the first cutting blade free end, and an atraumatic blunt surface along the leading side of the first cutting blade. The second cutting blade has a second cutting edge extending along a leading side of the second cutting blade whereby the first and second cutting edges face one another.

The first and second cutting blades are supported at the distal ends of respective first and second shaft members. In a retracted position, the second cutting blade is spaced proximally from the first cutting blade as the blunt distal leading blade side is applied against the exterior surface of the vessel wall to depress the vessel wall and is moved laterally to pass the cutting tip of the first cutting blade through the vessel wall and into the lumen of the body vessel. The first and second shaft members are moved together to bring the first and second cutting edges substantially in side-by-side alignment to shear the vessel wall therebetween and form a slit therein.

In preferred embodiments, the elongated instrument shaft comprises a fixed shaft member and a movable shaft member. A fixed cutting blade is fixed to the fixed shaft member at the shaft distal end to extend substantially orthogonally or laterally to the shaft axis to a fixed cutting blade free end. The fixed cutting blade has a blunt distal or leading blade side, a fixed cutting edge extending along the proximal or trailing blade side, and a sharpened point or tip at the fixed cutting blade free end. The movable shaft member supports a movable cutting blade extending substantially laterally to the shaft axis and having a movable cutting edge along the movable cutting blade distal or leading edge. The movable shaft member is supported for movement with respect to the fixed shaft member between a retracted position separating the fixed and movable cutting edges and an advanced or extended position wherein the fixed and movable cutting edges are substantially in side-by-side alignment.

In preferred embodiments, the movable shaft member comprises a plunger extending through a lumen of the fixed shaft member, and the movable shaft member is maintained in the retracted position by a spring extending between the fixed and movable shaft members exerting a retraction force. The plunger is movable to the advanced or extended position by force applied to the plunger proximal end that overcomes the retraction force.

In one preferred embodiment, the proximal end of the plunger is coupled to a distal end of a flexible cable extending proximally through a flexible tube to a remote plunger. The surgeon can position the fixed cutting blade against and move it into the body vessel with one hand and can grasp and depress the remote plunger with the other hand to move the movable cutting blade past the fixed cutting blade to cut the slit through the vessel wall.

In another preferred embodiment, the plunger proximal end is coupled to the trigger of a handle and is moved distally against the spring force by operation of the trigger. The handle is mounted to the fixed shaft member at the shaft proximal end and is grasped in use by the surgeon. The surgeon can position the fixed cutting blade into engagement against the body vessel and insert it into the vessel lumen and can then move the movable cutting blade past the fixed cutting blade with one hand to cut the slit through the vessel wall.

These embodiments of the invention may be employed to form the incision or slit of an arteriotomy in a coronary artery and source vessel while the heart is beating and/or through minimally invasive incisions and ports inserted through such incisions. Such ports may comprise structures for applying stabilizing force or suction against the area of the heart surrounding or alongside the coronary artery during use of the cutting instrument or to compress the artery lumen and inhibit blood loss through the elongated slit.

In further embodiments, pressure or suction applying tissue stabilization and/or vessel occlusion structures are employed with or incorporated with the elongated instrument shaft to applying stabilizing force or suction against the area of the heart surrounding or alongside the coronary artery during use of the cutting instrument or to compress the artery lumen and inhibit blood loss through the elongated slit.

These embodiments of the invention can be advantageously employed in a method of making an elongated slit through a vessel wall and into a lumen of a body vessel of a patient after obtaining access to an exposed surface of the vessel wall through an incision or port fitted through an incision. The elongated instrument shaft is advanced therethrough to dispose the fixed cutting blade in substantially axial alignment with the axis of the body vessel. Suction and/or mechanical pressure can be applied to stabilize of the tissue adjacent to the exposed surface of the body vessel wall or an occluding structure can be applied across the body vessel.

The blunt leading side of the fixed cutting blade is applied against the surface of the vessel wall in substantially parallel alignment with the body vessel axis with sufficient force to depress the vessel wall, so that the vessel wall wells up and against the tip of the fixed cutting blade. The fixed cutting blade is then moved in the direction of the body vessel axis to pass the tip of the fixed cutting blade through the vessel wall. In this way, the vessel wall is penetrated with the cutting tip of the fixed cutting blade pointing in the direction of the vessel axis and directed into the lumen of the body vessel, and the potential of penetrating the opposite vessel wall by the cutting tip is minimized.

The movable shaft member is then advanced distally with respect to the fixed shaft member to move the movable cutting edge past the fixed cutting edge and shear the vessel wall therebetween to form the elongated slit through the vessel wall. The slit has a precise length determined by the length of the cutting edges of the fixed and movable cutting blades.

The present invention advantageously provides a vessel wall cutting tool or instrument and method for making an arteriotomy in an artery or a similar slit in a vessel wall of a desired length though a minimally invasive incision and that does not inadvertently damage the vessel wall opposite to the slit.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 7A-7F are schematic illustrations of the sequence of steps to create an elongated incision through a vessel wall, e.g., an arteriotomy in the exterior vessel wall of a coronary artery;

FIGS. 8A-8F are schematic illustrations of variations of the shape of the movable cutting blade of the vessel wall cutting instrument;

FIG. 9 is a schematic illustration of the application of the vessel wall cutting instrument of the invention to the exposed exterior surface of the wall of a coronary artery in accordance with the step illustrated in FIG. 7B to create an arteriotomy as an area of the beating heart including the coronary artery is immobilized by suction applied to the epicardium and extending alongside the artery;

FIG. 10 is a schematic illustration of the application of the vessel wall cutting instrument of the invention to the exposed exterior surface of the wall of a coronary artery in accordance with the step illustrated in FIG. 7B to create an arteriotomy as an area of the beating heart including the coronary artery is immobilized by force applied through pads applied to the epicardium and extending alongside the artery;

FIG. 12 is a schematic illustration of the application of a further embodiment of a vessel wall cutting instrument of the invention applied to the exposed outer surface of the wall of a coronary artery to create an arteriotomy as an area of the beating heart is immobilized and the vessel occluded by a frame applied to the epicardium extending alongside and across the artery;

FIG. 13 is a side view of a first preferred embodiment of a vessel wall cutting instrument of the present invention with the movable cutting blade in the retracted position;

FIG. 14 is a cross-section view taken along lines 14-14 of FIG. 13 depicting the internal components of the first preferred embodiment of a vessel wall cutting instrument of the present invention;

FIG. 15 is a side view of the first preferred embodiment of a vessel wall cutting instrument of the present invention with the movable cutting blade in the extended position;

FIG. 16 is a cross-section view taken along lines 16-16 of FIG. 15 depicting the internal components of the first preferred embodiment of a vessel wall cutting instrument of the present invention;

DETAILED DESCRIPTION OF THE PREFERRED EMBODIMENTS

In the following detailed description, references are made to illustrative embodiments for carrying out the invention. It is understood that other embodiments may be utilized without departing from the scope of the invention.

For example, while a preferred method of forming arteriotomies in a coronary artery and a source vessel in the process of performing a coronary artery anastomosis in a thoracoscopic CABG procedure will be described herein, it is to be understood that the principles of the present invention may be applied to a wide variety of surgical procedures, both conventional, open chest procedures, as well as minimally invasive, closed chest procedures, to form precise elongated slits in vessel walls.

Vessel wall cutting instruments of the present invention are employed to efficiently form "perfect arteriotomies" in vessel walls through the passage of the lower blade of the instrument into the lumen of the vessel and lowering the upper blade of the instrument past the lower blade thereby cutting the tissue between. The close passage of the cutting edges of the two blades against one another shears the tissue between the two resulting in a perfect arteriotomy.

In accordance with the present invention, vessel wall cutting instruments and associated instruments and methods are provided that can be used in any of the above described full exposure surgical procedures or less invasive MIDCAB or percutaneous exposures of the vessels in question, particularly, the above-described CABG procedures on a stopped or beating heart.

Figure 1:
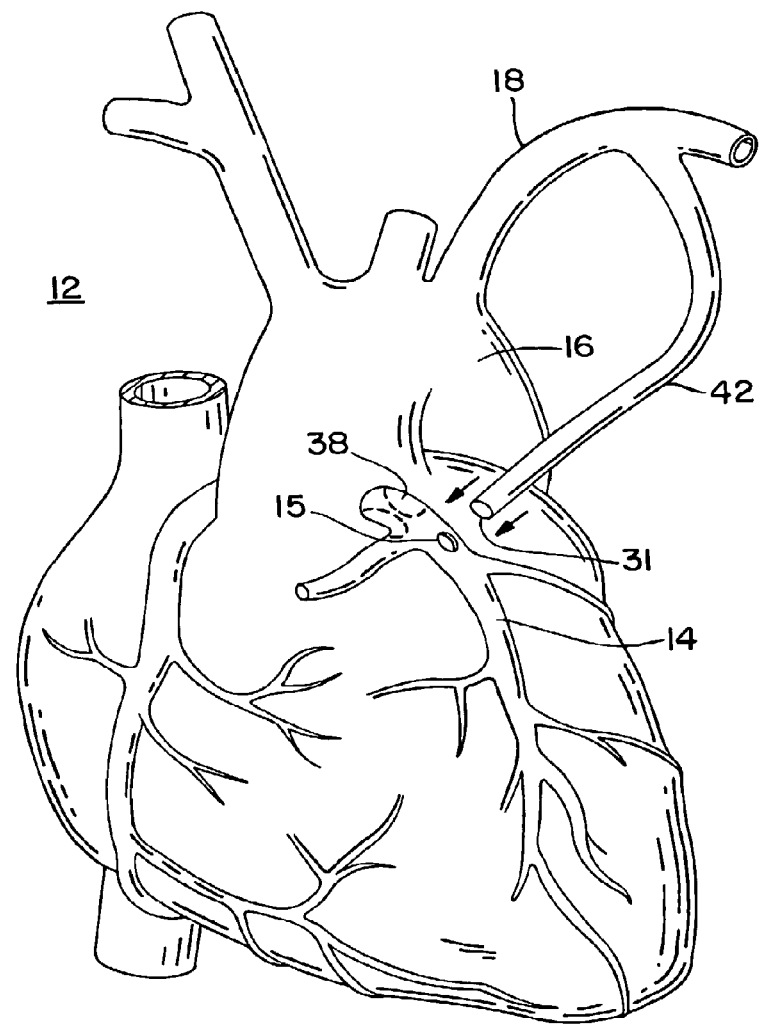
FIG. 1 is a schematic illustration of the preparation of a source vessel free end and an arteriotomy in a coronary artery downstream from an obstruction for an end-to-side anastomosis.
Figure 2:
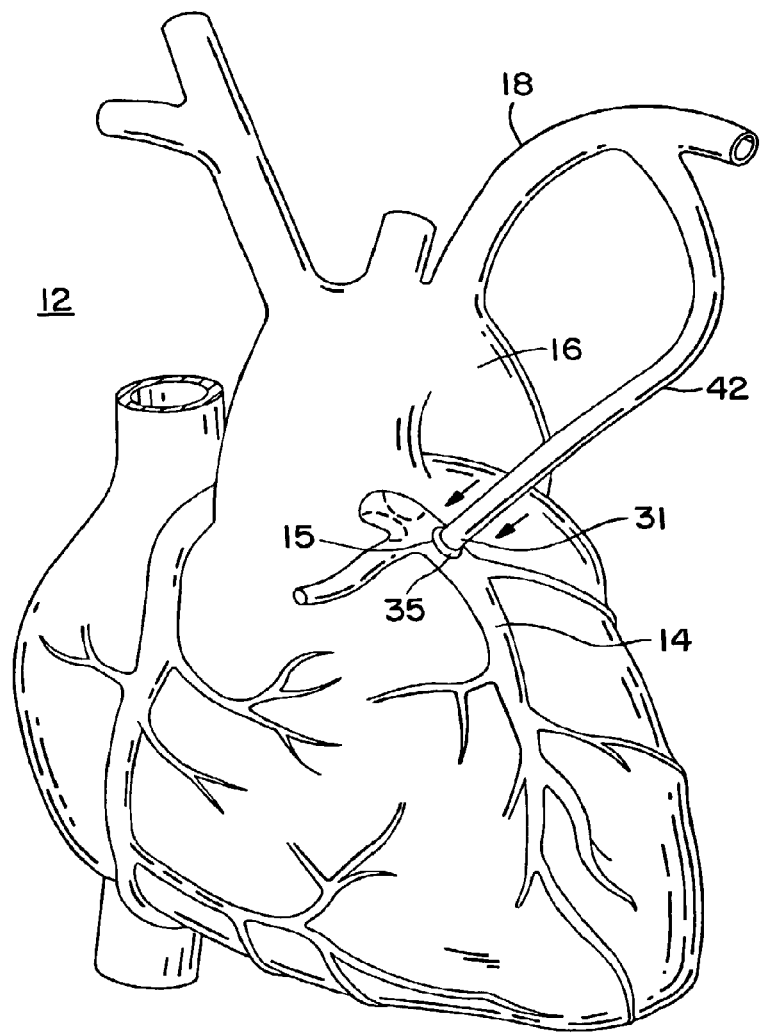
FIG. 2 is a schematic illustration of the end-to-side anastomosis of the source vessel free end to the arteriotomy in the coronary artery.
Figure 4:
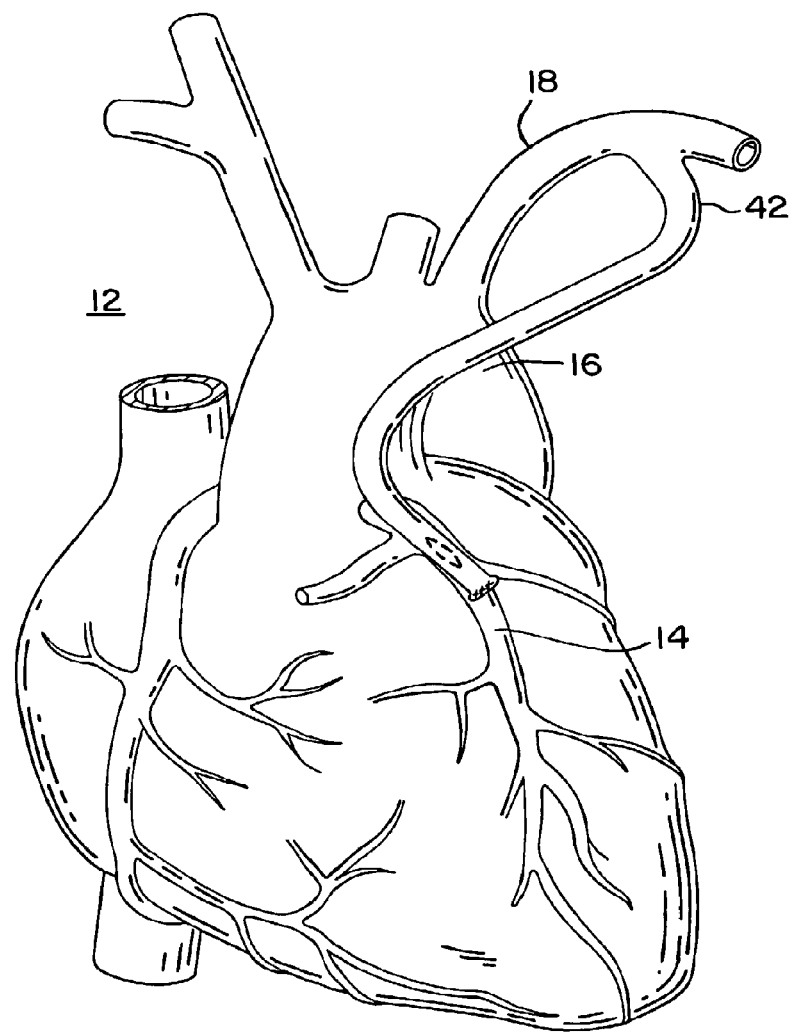
FIG. 4 is a schematic illustration of the side-to-side anastomosis of the arteriotomy in the source vessel to the arteriotomy in the coronary artery.
Figure 5:
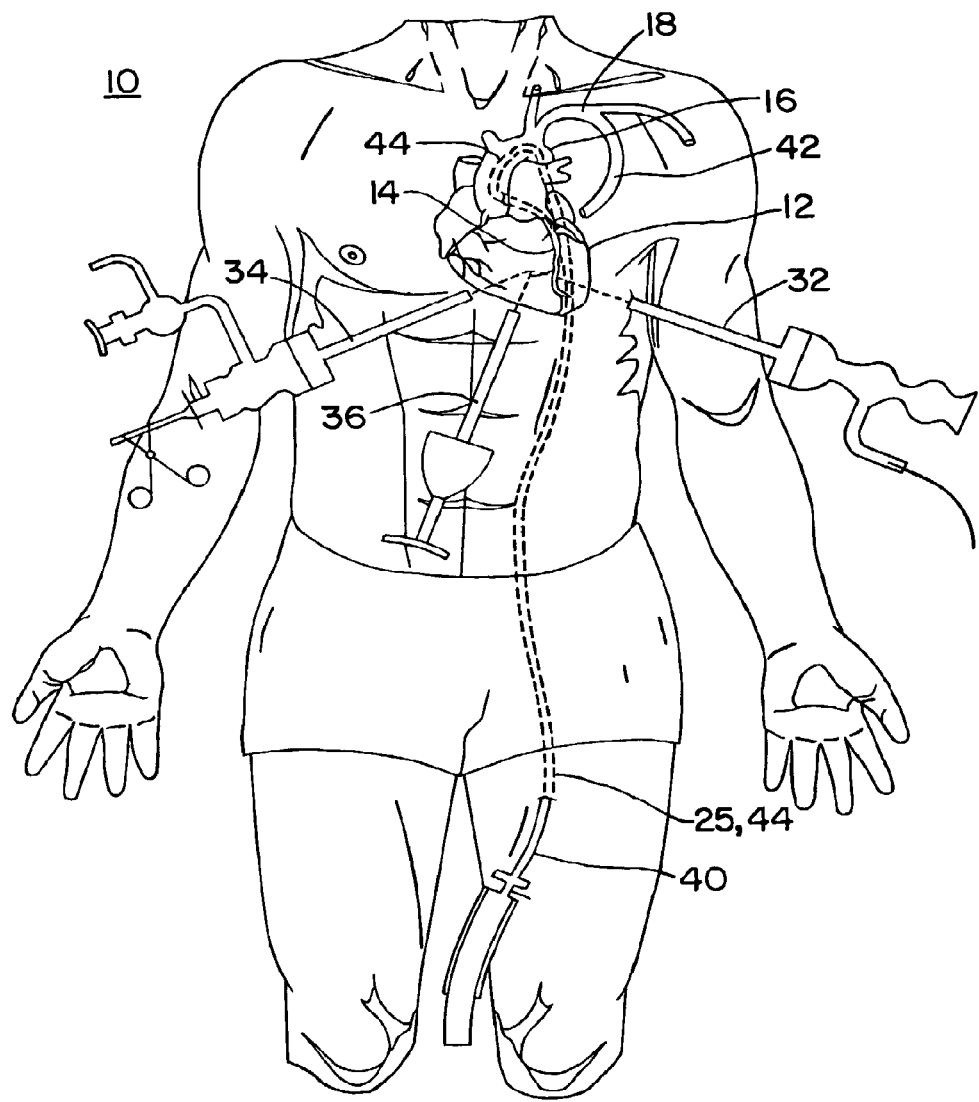
FIG. 5 is an illustration of the preparation of a patient for a percutaneous CABG procedure and particularly the determination of a suitable anastomosis site in a coronary artery.

Exemplary Percutaneous Surgical Exposure:

Thus, for example, FIG. 5 depicts the preparation of the patient 10 for a CABG procedure performed percutaneously and advantageously while the heart 12 is beating. Percutaneous access to the blocked coronary artery and source vessel as well as intra-arterial access into the arterial lumens to effect an artery-to-artery CABG procedure are depicted in FIG. 5. Mechanical instruments and methods of the present invention are employed to make the arteriotomy 15 in the side-wall of the LAD coronary artery 14 distal to the site of an obstruction 38 for either of the end-to-side vascular anastomosis as depicted, for example, in FIGS. 1 and 2 or the side-to-side vascular anastomosis as depicted, for example, in FIGS. 3 and 4 and, in the latter procedure, the arteriotomy 33 in the side wall of the freed end portion of the left IMA 30.

It will be understood that an angiography of the coronary arteries of the heart of the patient 10 has been completed to identify the obstruction 38 in the LAD coronary artery 14. Typically, the surgeon will already have an angiogram of the affected coronary artery available as a result of the earlier diagnosis of the necessity for the coronary bypass.

The patient 10 is placed under general anesthesia, and the patient's left lung is deflated using conventional techniques. The patient 10 is placed in a lateral decubitus position on his right side, and multiple small percutaneous incisions are to be made in the chest wall for the receipt of surgical instruments. As used herein, the term "percutaneous" refers to any penetration through the skin of the patient, whether in the form of a small cut, incision, hole, cannula, trocar sleeve or port or the like. For example, two small incisions are made in the chest wall of patient 10 at different interstitial positions between the patient's ribs, while a third incision is made just below the sternum.

In certain procedures, the catheter body 44 of a femoral catheter 40 is introduced into the femoral artery 25 and advanced into the aorta 16 to locate the femoral catheter distal end at or within the ostium of the LAD coronary artery 14 as shown in FIG. 5. The surgeon identifies a suitable position for insertion of a Beress insufflation needle or other suitable needle based upon the pathology and anatomy of the patient 10. Typically, this needle will be inserted between the fifth or sixth intercostal space along the anterior axillary line and into the region between the parietal pleura and the pericardium. The parietal pleura and pericardium are then separated, and the Beress needle is removed.

A first trocar (not shown) having a cutting tip is inserted in the lumen of port 32 having a diameter of approximately 8 to 12 mm and, preferably, 10 mm, and the assembly is then inserted into the thoracic cavity along the same path traveled by the Beress insufflation needle. The trocar is then removed from port 32 and a conventional endoscopic telescope or thoracoscope (not shown) is introduced through the port 32 into the thoracic cavity. This thoracoscope is used to directly visualize the thoracic cavity and obtain a left lateral view of the pericardial sac or pericardium over the heart 12.

The surgeon determines the best locations for insertion of the assembly of a second trocar (not shown) and port 34 and the assembly of a third trocar (not shown) and port 36 based upon direct visualization through the thoracoscope of the pericardium overlying the heart 12, the presumed locations of the coronary artery of interest and the source artery as well as the anatomy and pathology of the patient 10 may be determined through biplane fluoroscopy and an angiogram. Typically, the second trocar and port 34 is inserted through the intercostal wall and into the thoracic cavity, and the third trocar and port 36 is inserted through the subxyphoid space. Additional trocars or other instruments can be inserted percutaneously as necessary. Often, it will be advantageous to insert a fourth trocar and port for introducing a clipping or suturing device into the thoracic cavity. In each case, the trocars are removed leaving the ports in place.

The parietal pleura is dissected and the pericardial sac is opened by instruments introduced through the second port 34 and/or the third port 36 using conventional techniques while visualizing the site through the thoracoscope. The thoracoscope is used to view the LAD coronary artery 14, in this case, to the extent that it can be seen because of overlying fatty tissue, and the location of the source artery, left IMA 42 in this case.

Figure 3:
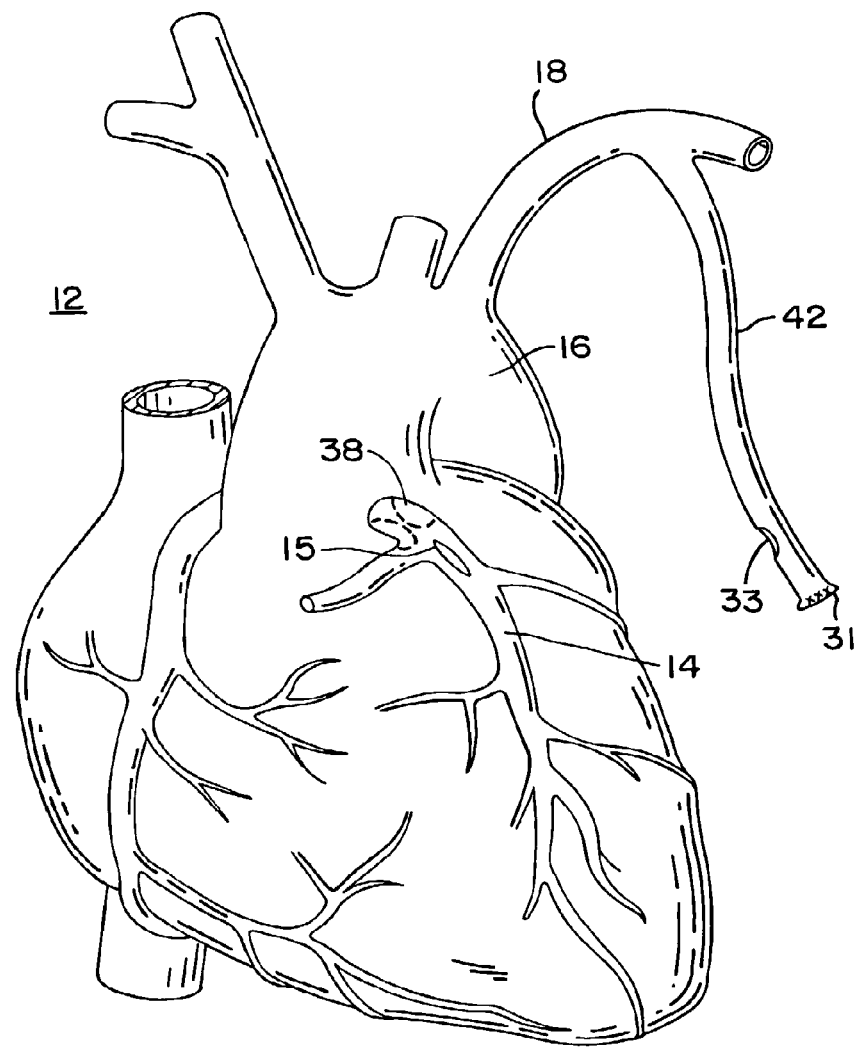
FIG. 3 is a schematic illustration of the preparation of a source vessel free end and an arteriotomy in a coronary artery downstream from an obstruction for a side-to-side anastomosis.

At this juncture, the LAD coronary artery 14 is identified, the location of the occlusion 38 is ascertained, and fatty tissue is dissected away at the proximal and/or distal sites of anastomosis. A distal portion of the left IMA 42 is dissected and freed from tissue as described above. The left IMA distal end 31 is shaped in preparation for the end-to-side anastomosis of FIGS. 1 and 2 or the arteriotomy 33 of FIGS. 3 and 4 is performed employing the mechanical instruments and methods described in detail herein in preparation for the side-to-side anastomosis.

Arteriotomy Instruments and Techniques:

In the examples of the practice of the present invention, the vessel wall cutting instruments of the present invention are employed as a mechanical arteriotomy forming instrument. A vessel wall cutting instrument 60 schematically illustrated in FIGS. 6-8, which can be of one of the types described further herein, is inserted through one of the ports 34 or 36 or FIG. 5 and the opening in the pericardial sac as shown schematically in FIG. 6.

The vessel wall cutting instrument 60 comprises an elongated instrument shaft 62 extending between an instrument shaft proximal end 64 adapted to be manipulated outside the body and a shaft distal end 66 and having a shaft axis 68. A vessel wall cutting head 70 is disposed at the shaft distal end 66. The elongated instrument shaft 62 preferably comprises a fixed shaft member 72 and a movable shaft member 82.

A first or fixed cutting blade 74 is fixed to the fixed shaft member 72 at the shaft distal end 66 to extend substantially orthogonally or laterally to the shaft axis 68 to a fixed cutting blade free end. The fixed cutting blade 74 has a blunt distal or leading blade side 76 and a fixed cutting edge 78 extending along the proximal or trailing blade side and terminating in a sharpened point or tip 80 at the fixed cutting blade free end.

The instrument shaft 62 further comprises the movable shaft member 82 coupled at its distal end to a second or movable cutting blade 84 extending substantially laterally to the shaft axis 68 and having a movable cutting edge 88 along the movable cutting blade distal or leading edge. The movable shaft member 82 is supported for movement with respect to the fixed shaft member 72 between a retracted position separating the fixed and movable cutting edges 78 and 88 and an advanced or extended position wherein the fixed and movable cutting edges 78 and 88 are substantially in side-by-side alignment. The cutting edges shear the vessel wall when the fixed and movable cutting edges 78 and 88 are brought substantially into side-by-side alignment.

The fixed and movable cutting edges 78 and 88 of the vessel cutting instrument 60 employed in making an arteriotomy are preferably about 3-5 mm in length to make a corresponding 3-5 mm long arteriotomy 15.

Figure 6:
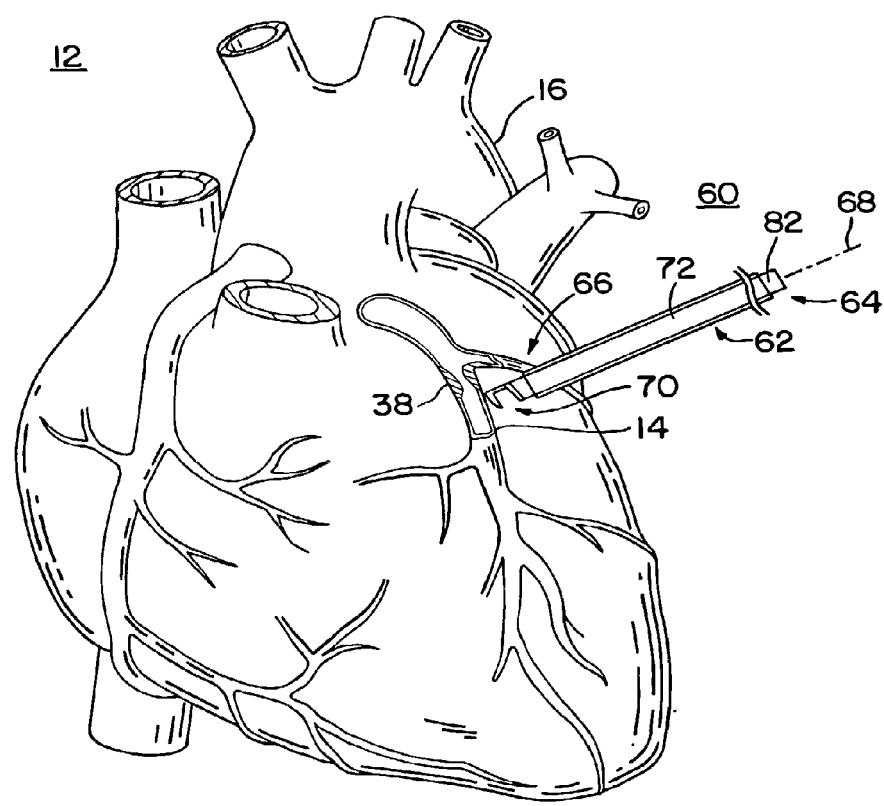
FIG. 6 is a schematic illustration of the application of the mechanical cutting instrument of the present invention to the exterior vessel wall of a coronary artery.

In use, the vessel wall cutting instrument 60 is advanced through an incision into the thoracic cavity, e.g. one of the ports 34 and 36 under visualization employing a thoracoscope extending through port 32 as shown in FIG. 5. The blunt leading edge 76 of the fixed cutting blade 72 is directed toward the epicardium and a site of the artery 14 as shown in FIG. 6. The beating heart 12 can stabilized or stilled in the area surrounding or beside site of the artery 14 in which the arteriotomy 15 is to be formed employing one of the stabilization embodiments of the port or vessel wall cutting instrument 60 described herein.

The axis 68 of the elongated vessel wall cutting instrument 60 is centered over the exposed exterior surface 26 of the arterial wall 22 and aligned to the axis 20 of LAD coronary artery 14 at the arteriotomy site downstream from the obstruction 38 (see FIG. 6 and FIG. 7a). The elongated instrument shaft 62 is advanced to dispose the fixed cutting blade 76 in substantially axial alignment with the axis 20 of the artery 14.

As shown in FIG. 7B, the blunt leading side 76 of the fixed cutting blade 74 is applied against the surface 26 of the arterial wall 22 in substantially parallel alignment with the artery axis 20 with sufficient force to depress the arterial wall 22 against the tip 80 of the fixed cutting blade 74. The arterial wall 22 bulges around the fixed cutting blade 74 and against the cutting tip 80. The fixed cutting blade 74 is then moved laterally in the direction of the artery axis 20 to pass the tip 80 of the fixed cutting blade 74 through the arterial wall 22 as shown in FIG. 7C. In this way, the arterial wall 22 is penetrated at perforation 30 as the cutting tip 80 of the fixed cutting blade 74 is moved axially into the lumen 24 of the artery 14. In this way, the potential of penetrating the arterial wall 22 opposite to the perforation 30 by the cutting tip 80 is minimized. Moreover, minimal tilting of the instrument shaft 62 at the shaft proximal end 64 is necessary to effect the perforation 30.

The elongated instrument shaft 62 can then be lifted or moved proximally through the incision from the shaft proximal end 64 to dispose the fixed cutting edge 78 against or alongside the interior surface 28 of the arterial wall 22 as shown in FIG. 7D The movable shaft member 82 is then advanced distally with respect to the fixed shaft member 72 as shown in FIG. 7E to move the movable cutting edge 88 alongside and past the fixed cutting edge 78 to form the slit or arteriotomy 15. However, it is not always necessary to lift and tension the arterial wall 22 in the steps illustrated in FIGS. 7D and 7E to make the slit 15. In practice, the 3-5 mm long arteriotomy 15 is cleaner and easier to make without tensioning the arterial wall 22 with the fixed shaft member 72.

Advantageously, the movable shaft member 82 can be advanced distally with respect to the fixed shaft member 72 as shown in FIG. 7E to make the arteriotomy 15 at any time during the heart cycle, and not necessarily while the heart is still in the relaxation interval between successive contractions. The arterial wall 22 is thereby sheared or slit to form the elongated arteriotomy 15 as shown in FIG. 7F, and the vessel wall cutting instrument 60 is withdrawn from the incision. The arteriotomy 15 has a precise length determined by the length of the cutting edges 78 and 88 of the fixed and movable cutting blades 74 and 84, respectively. The same process may be employed to form slits in other body vessels including other blood vessels.

Figure 21:
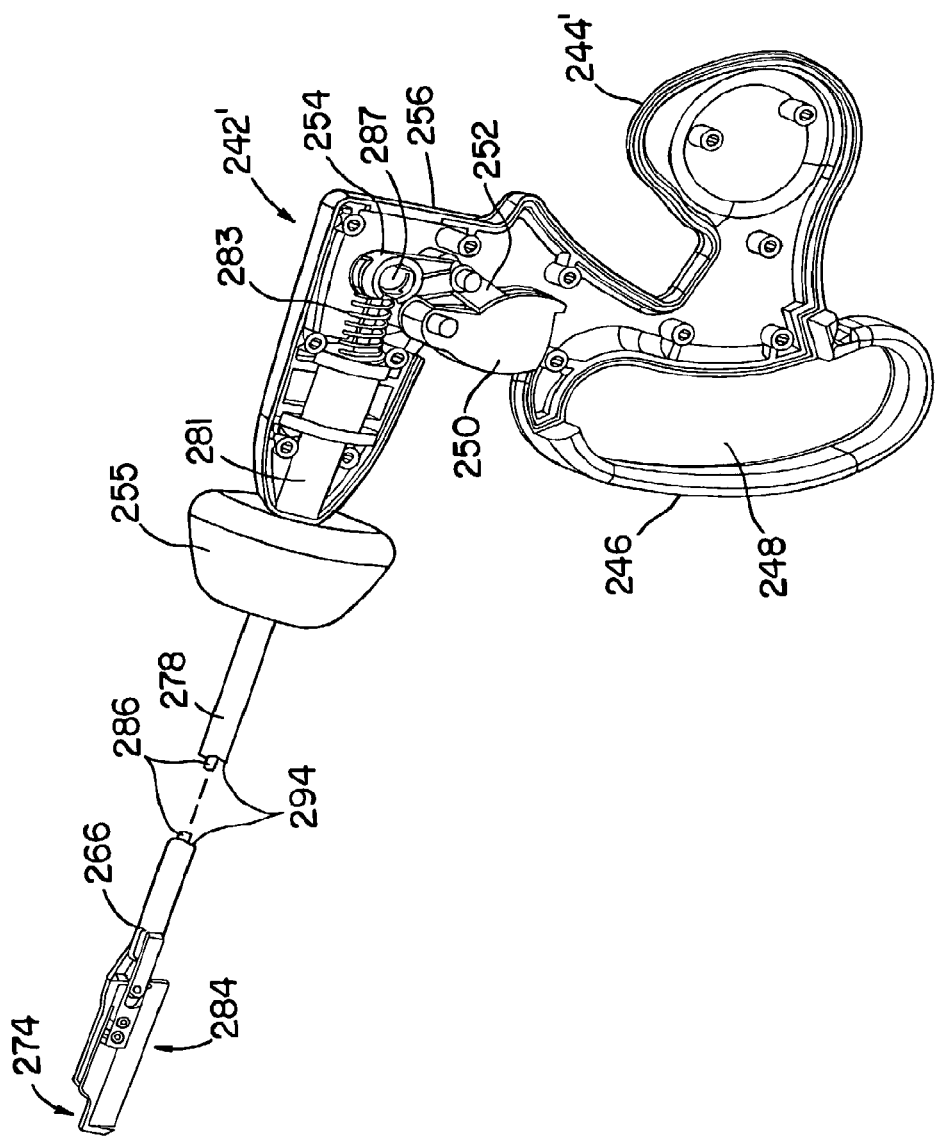
FIG. 21 is a partial perspective view of the proximal portion of the third preferred embodiment of the vessel wall cutting instrument FIG. 19 with the movable cutting blade in the extended position.

It will be understood that the movable cutting edge 88 of the movable cutting blade 84 can take a variety of shapes. The movable cutting edge 88 is angled with respect to the fixed cutting edge 78 to extend toward the tip 80 as shown FIGS. 6 and 7A-7F. An alternative movable cutting edge $88_1$ extending substantially parallel to the fixed cutting edge 78 is shown in FIG. 8A. A further alternative, angled, movable cutting edge $88_2$ extending away from the tip 80 is shown in FIG. 8B. Further alternative movable cutting edges $88_3$ and $88_4$ shaped like an inverted and upright chevrons, respectively, are depicted in FIGS. 8C and 8D. Still further alternative, convex and concave, movable cutting edges $88_5$ and $88_6$ are depicted in FIGS. 8E and 8F, respectively. The movable cutting edge 88 in all of these variations is beveled on the side away from the fixed cutting edge 78 to a sharp edge (as also shown in FIG. 21) that bears against and slides along and past the fixed cutting edge 78 as the movable cutting edge 88 is moved to the advanced or extended position of FIG. 7E.

Cutting or scraping of adjacent tissue is advantageously limited or prevented through the particular designs of the fixed and movable cutting edges 78 and 88 through $88_6$. The procedure illustrated in FIGS. 7A-7F provides a clean cut at arteriotomy 15 without damage to adjacent tissue. A clean, controlled cut of a prescribed length in axial alignment with the vessel axis is particularly desirable to assure that tearing does not occur in a direction away from the desired orientation of the cut.

It will be understood that while the second or movable cutting blade 84 is moved distally as shown in FIG. 7E, alternatively, the distal or first (fixed) and the proximal or second (movable) cutting blades 74 and 84 can be both mounted on movable shaft members enabling simultaneous movement toward one another to be brought into side-by-side relation as shown in FIG. 7E. Similarly, the distal cutting blade 74 could be mounted to a movable shaft member and the proximal cutting blade 84 could be mounted to a fixed shaft member, whereby the distal cutting blade 74 is moved (thereby designated a second or movable cutting blade in the context of terminology of the invention) while the proximal cutting blade 84 is fixed (thereby designated a first or fixed cutting blade in the context of terminology of the invention).

Stabilization:

The above-described electrosurgical vessel wall cutting instrument 60 and method of use and equivalents thereto, can be employed in CABG procedures that are conducted while the heart is either arrested or beating. When the heart is beating, it may be preferable to employ further heart stabilization tools and techniques to stabilize the heart around the site of the arteriotomy 15 in LAD coronary artery 14 and to minimize blood loss through the arteriotomy. To this end, any of the instruments and techniques for applying pressure against the epicardial surface can be employed, e.g., the instruments mounted to the retractors maintaining the chest wall incision and the techniques disclosed in the above-referenced '782 patent. Or, a frame of the type described in the above-referenced '069 patent can be temporarily sutured to or held against the epicardium to immobilize the area and compress the artery lumen and inhibit blood loss through the elongated slit.

Alternatively, suction can be applied to the epicardial surface as shown for example in the above-referenced '295 patent or in commonly assigned U.S. Pat. No. 6,394,948 and PCT Publication WO 02/28287 wherein the instruments and suction elements are mounted to the surgical table or another stable platform. The Octopus® flexible tissue stabilization system sold by assignee of the present application can be employed to grip and stabilize or immobilize the epicardial surface tissue on either side of the site of a vessel wall where an elongated slit is to be made.

Thus, the use of such a tissue stabilization system 400 to stabilize or immobilize the epicardial surface tissue on either side of the site of the arteriotomy 15 in LAD coronary artery 14 is illustrated schematically in FIG. 9. An articulating or flexible arm 404, 406, is attached to a fixed reference 402, which can be a retractor affixed to an opening in the patient's chest wall or other operating room equipment, e.g., an operating table. A vacuum source is coupled to a lumen of the arm 406 or to flexible tubing (not shown) that in either case extends into the interior manifolds of stabilizer suction pads 410 and 414 that extend on either side of the site of the arteriotomy 15. In this example, the stabilizer suction pads 410 and 414 are formed as described in the above-referenced PCT Publication WO 02/28287, for example. A plurality of suction ports 412 and 416 extend through surfaces of the suction pads 410 and 414, respectively that are applied against the epicardial surface from manifolds within the suction pads 410 and 414. In this illustrated embodiment, the manifolds within the suction pads 410 and 414 are coupled through an air passage within joint 408 to a suction tube or lumen of the arm 406 that extends to a vacuum port (not shown). Instead, flexible tubing could be employed as in the Octopus® flexible tissue stabilization system to apply suction from the vacuum source directly into each of the manifolds within the suction pads 410 and 414. It will be understood that a single horseshoe shaped or rectilinear suction pad could be substituted for the pair of stabilizer suction pads 410 and 414.

In use, the stabilizer suction pads 410 and 414 are lined up with the axis of the LAD coronary artery 14 (or other target vessel). The vacuum source creates suction between the epicardium and the suction pads 410 and 414 to minimize heart movement in the area around the site of the arteriotomy. The stabilizer suction pads 410 and 414 can be spread apart in the manner of the Octopus® flexible tissue stabilization system to further immobilize the tissue area around the site of the arteriotomy 15.

The vessel wall cutting instrument 60 and the particular embodiments described herein and equivalents thereto can be applied to the artery 14 to form the arteriotomy 14 as described above while the tissue area of the heart is stabilized.

It is also contemplated that the above-described vessel wall cutting instrument 60 can be inserted through the lumen of a stabilization port that incorporates heart stabilization devices, e.g., suction pads and/or pressure applying feet applied against the epicardium alongside the artery or frames applied against the epicardium alongside the artery and extending across the artery to compress the artery lumen and inhibit blood loss through the elongated slit.

In one embodiment, a stabilization port 440 illustrated in FIG. 10 comprises an elongated tubular port shaft 444 having a port lumen 448 extending to a distal lumen end opening 442. The port 440 further comprises a pair of stabilizer feet 452 and 454 coupled to the elongated tubular port shaft 444 at junction 446. A vessel wall cutting instrument 60 is depicted in FIG. 10 inserted through the port lumen 448 so that the fixed cutting blade 74 extends through the distal end opening 442 and substantially transversely to the axis of the port shaft 444.

In use, the surgeon manipulates the port 440 to apply the stabilizer feet 452 and 454 against the epicardium and manipulates the vessel wall cutting instrument 60 to align the upper and lower cutting blades 74 and 84 with the arterial axis centered over exposed wall of the LAD coronary artery 14 at the site where an arteriotomy is to be made. The surgeon applies pressure through the tool body 444 to press the stabilizer feet 452 and 454 against the epicardium and to the vessel wall cutting instrument 60 to press the fixed cutting blade 74 against the arterial wall in accordance with step 7B prior to making an arteriotomy through the arterial wall. The surgeon then completes the steps illustrated in FIGS. 7C and 7D while heart movement is minimized in the area around the site of the arteriotomy by the applied pressure. The arteriotomy is formed pursuant to the cutting step illustrated in FIG. 7E in the interval between heart contractions.

The insertion of the of the lower cutting blade 74 into the arterial lumen in the step illustrated in FIG. 7C can be completed by laterally moving the shaft proximal end if the diameter of the port lumen 448 is sufficiently greater than the diameter of the elongated instrument shaft 62. Alternatively, it is possible to release pressure and/or suction in order to insert or complete the insertion of the fixed cutting blade 74 into the arterial lumen in the step illustrated in FIG. 7C by moving both the vessel wall cutting instrument 60 and the stabilization port 440. The arteriotomy 15 is formed pursuant to the cutting step illustrated in FIGS. 7E and 7F.

Figure 11:
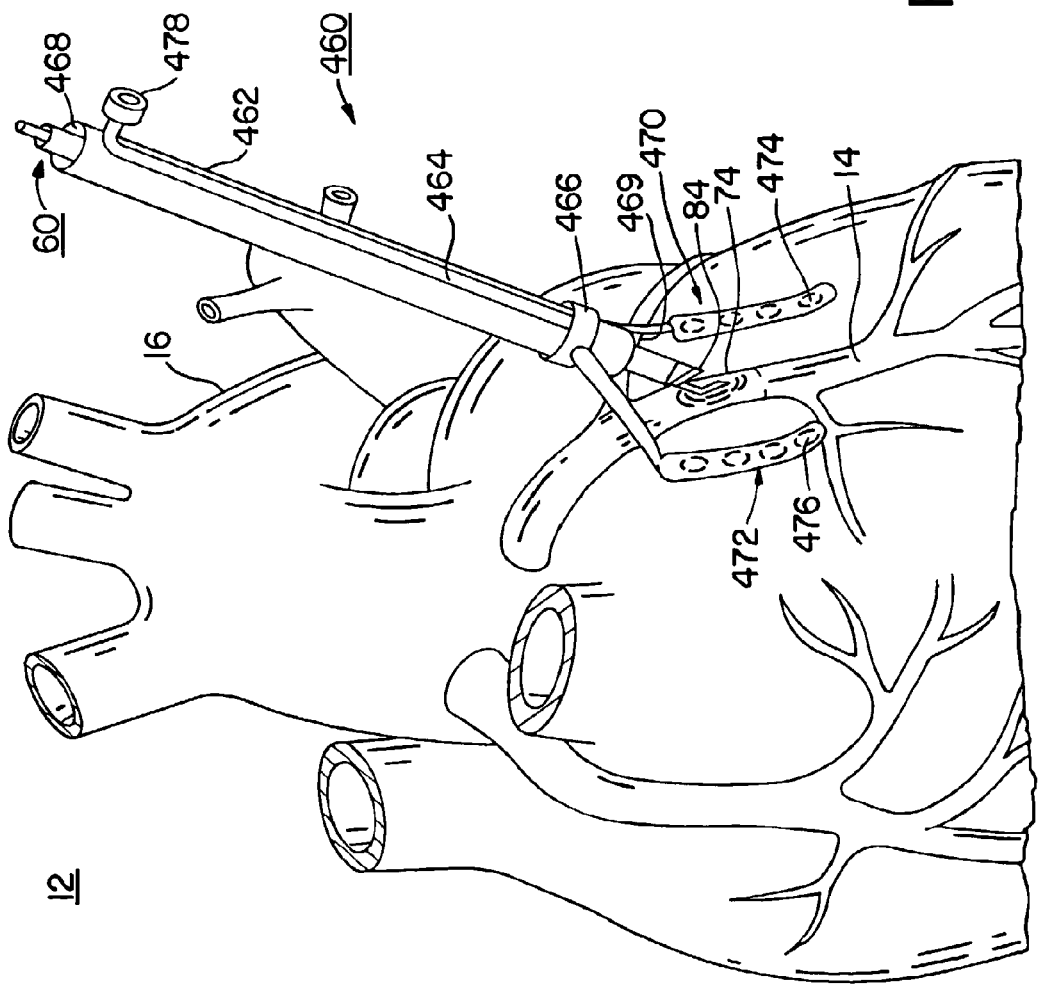
FIG. 11 is a schematic illustration of the application of the vessel wall cutting instrument of the invention to the exposed exterior surface of the wall of a coronary artery in accordance with the step illustrated in FIG. 7B to create an arteriotomy as an area of the beating heart including the coronary artery is immobilized by suction applied through suction pads applied to the epicardium and extending alongside the artery.

In a further embodiment, a stabilization port 460 illustrated in FIG. 11 comprises an elongated tubular port shaft 462 having a port lumen 468 extending to a distal lumen end opening 469. The port 460 further comprises a pair of elongated suction pads 470 and 472 coupled to the elongated tubular port shaft 462 at a manifold 466. It will be understood that a single horseshoe shaped or rectilinear suction pad could be substituted for the pair of stabilizer suction pads 470 and 472. A suction line or lumen 464 extends from the manifold 466 to a suction port 478 adapted to be coupled to a vacuum source through a valve (not shown). A vacuum drawn through the suction port 478 causes suction to be applied to the epicardium through suction ports 474 and 476 along the suction pads 470 and 472, respectively, if the suction pads are applied against the epicardium. A vessel wall cutting instrument 60 is depicted in FIG. 11 inserted through the port lumen 448 so that the fixed cutting blade 74 extends through the distal end opening 442 and is applied against the wall of LAD coronary artery 14 in accordance with step 7B prior to making an arteriotomy through the arterial wall.

In use, the surgeon manipulates the port 460 to apply the suction pads 470 and 472 against the epicardium and operates the valve to apply suction to the epicardium to stabilize the area between the suction pads 470 and 472 including a section of the LAD coronary artery 14. The surgeon also manipulates the vessel wall cutting instrument 60 to align the upper and lower cutting blades 74 and 84 with the arterial axis centered over exposed wall of the LAD coronary artery 14 at the site where an arteriotomy is to be made. The surgeon applies pressure to the vessel wall cutting instrument 60 to press the fixed cutting blade 74 against the arterial wall in accordance with step 7B prior to making an arteriotomy through the arterial wall. The surgeon then completes the steps illustrated in FIGS. 7C and 7D while heart movement is minimized in the area around the site of the arteriotomy by the applied pressure.

The insertion of the of the lower cutting blade 74 into the arterial lumen in the step illustrated in FIG. 7C can be completed by laterally moving the shaft proximal end if the diameter of the port lumen 468 is sufficiently greater than the diameter of the elongated instrument shaft 62. Alternatively, it is possible to release pressure and/or suction in order to insert or complete the insertion of the fixed cutting blade 74 into the arterial lumen in the step illustrated in FIG. 7C by moving both the vessel wall cutting instrument 60 and the stabilization port 460. The arteriotomy 15 is formed pursuant to the cutting step illustrated in FIGS. 7E and 7F.

It is also desirable to both stabilize the area of the heart about the arteriotomy site and to occlude the target artery lumen upstream and downstream of the arteriotomy site. The stabilization port 480 illustrated in FIG. 12 comprises an elongated tubular port shaft 484 having a port lumen 488 extending to a distal lumen end opening 482. The port 480 further comprises a stabilization and vessel occluding frame 490 supported by the port shaft 484 applied around the site of the arteriotomy and across the LAD coronary artery 14. Frame struts 492 and 494 extend from the port shaft 484 to a rectilinear stabilization and vessel occlusion frame 490. Occlusion pads 496 and 498 extend distally from the frame 490 to compress the arterial wall and occlude the arterial lumen when the frame 490 is applied against the artery 14 and the epicardium. A vessel wall cutting instrument 60 is depicted in FIG. 12 inserted through the port lumen 448 so that the fixed cutting blade 74 extends through the distal end opening 442 and substantially transversely to the axis of the port shaft 444.

In use, the surgeon manipulates the port 480 to apply the frame 490 against the epicardium and the occlusion pads 496 and 498 against the artery 14 to occlude the artery 14. The surgeon also manipulates the vessel wall cutting instrument 60 to align the upper and lower cutting blades 74 and 84 with the arterial axis centered over exposed wall of the LAD coronary artery 14 at the site where an arteriotomy is to be made. The surgeon applies pressure through the tool body 484 to press the frame 490 against the epicardium and to the vessel wall cutting instrument 60 to press the fixed cutting blade 74 against the arterial wall in accordance with step 7B prior to making an arteriotomy through the arterial wall. The surgeon then completes the steps illustrated in FIGS. 7C and 7D while heart movement is minimized in the area around the site of the arteriotomy by the applied pressure.

The insertion of the of the lower cutting blade 74 into the arterial lumen in the step illustrated in FIG. 7C can be completed by laterally moving the shaft proximal end if the diameter of the port lumen 488 is sufficiently greater than the diameter of the elongated instrument shaft 62. Alternatively, it is possible to release pressure and/or suction in order to insert or complete the insertion of the fixed cutting blade 74 into the arterial lumen in the step illustrated in FIG. 7C by moving both the vessel wall cutting instrument 60 and the stabilization port 480. The arteriotomy is formed pursuant to the cutting step illustrated in FIG. 7E.

It will be understood that the features of the stabilization ports 460 and 480 can be combined such that suction ports are formed along frame 490 and a suction port and lumen are provided on port shaft 484 so that suction can be applied to the epicardium alongside or around the site of the arteriotomy.

It will also be understood that the stabilization ports 440, 460 and 480, and combinations of the features thereof, can be combined with the vessel wall cutting instrument 60 in a single structure.

Vessel Wall Cutting Instrument Embodiments

A first preferred embodiment of a vessel wall cutting instrument 160 having an elongated shaft 162 extending between shaft proximal and distal ends 164 and 166 is depicted in FIGS. 13-16. In this embodiment, the fixed shaft member 72 comprises an elongated tube 172 and a proximal retention cap 173. The retention cap 173 and elongated tube 172 are cylindrical at the instrument proximal end 164, and the elongated tube 172 is tapered at the shaft distal end 166. A lumen extends through the length of the elongated tube 172. The lumen includes a distal, rectilinear, lumen portion 194 and a proximal cylindrical lumen portion 195.

A vessel wall cutting head 170 is formed of a fixed cutting blade 174 and a movable cutting blade 184. A cutting blade mounting plate 175 is shown in FIGS. 14 and 16 fitted within the elongated tube 172 alongside the distal, rectilinear, lumen portion 195 and pinned to the elongated tube 172. A shank 177 extends distally from plate 175 to the laterally extending fixed cutting blade 174. The fixed cutting blade 174 is formed with the trailing fixed cutting edge 178, the leading blunt edge or side 176 and the cutting tip 180.

The movable shaft member comprises a plunger 182 extending through the fixed shaft member lumen 194 to the movable cutting edge 188 of movable cutting blade 184. The plunger 182 comprises a tubular proximal push-button 183 that is trapped by the retention cap 173 within the proximal cylindrical lumen portion 195, an elongated shaft 186, and a stop member 191. The elongated shaft 186 in this embodiment is elongated and flat or rectilinear comprising a rectilinear proximal portion 185 fitting within the proximal cylindrical lumen portion 195 and a rectilinear distal portion 187 that extends through the rectilinear lumen portion 197 terminating in the movable cutting blade 184. The proximal end of the proximal portion 185 is coupled to a tubular stop member 191 (shown in cross-section) that bears against, but is not attached to, the interior face of the push-button 182. A slot (not shown) is formed in the distally extending portion of the stop member 191, and the proximal end of the proximal portion 185 is fitted into the slot and pinned in the slot by a laterally extending pin 199

A coiled wire spring 190 is fitted around the proximal portion 185 of the elongated rectilinear shaft 186 within the proximal cylindrical lumen portion 195. The retraction force of the spring 190 biases the stop member 191, the push-button 183, and the movable cutting blade 184 proximally to retract and maintain the movable cutting edge 188 within the distal portion of rectilinear lumen 194 as shown in FIGS. 13 and 14. In use, the spring force of spring 190 is overcome by pressing the tubular proximal push-button 183 of plunger 182 distally while the proximal retention cap 173 and/or elongated tube are held steady to overcome the retraction force and push the movable cutting edge 188 alongside and past the fixed cutting edge 178 as shown in FIGS. 15 and 16.

Figure 17:
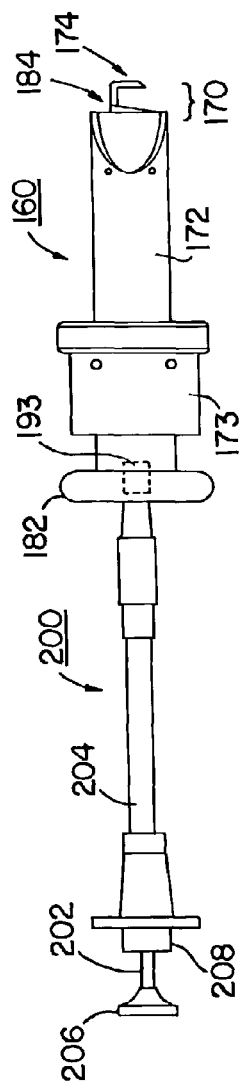
FIG. 17 is a side view of a second preferred embodiment of a vessel wall cutting instrument of the present invention with the movable cutting blade in the retracted position.
Figure 18:
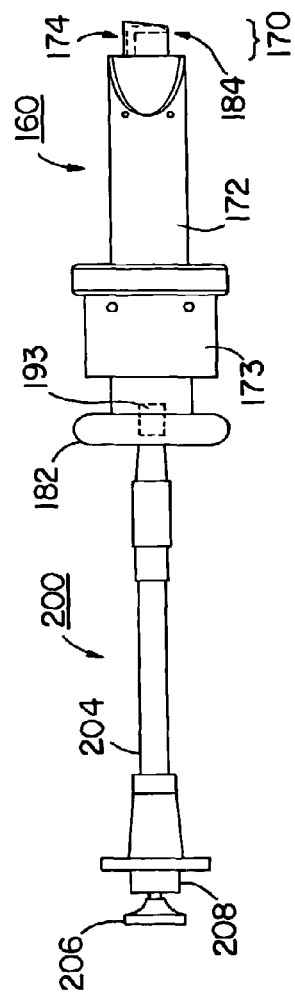
FIG. 18 is a side view of the second preferred embodiment of a vessel wall cutting instrument of FIG. 17 with the movable cutting blade in the extended position.

As shown in FIGS. 13-16, a hole 193 extends through the push-button 182 to the distal face of the stop member 191. In a variation of this preferred embodiment depicted in FIGS. 17 and 18, the vessel wall cutting instrument 160 is attached to and can be operated by a flexible remote control 200. The proximal end of the plunger 182 is coupled to a distal end of a flexible cable 202 extending proximally through the lumen of a flexible tube 204 to a remote plunger 206. In particular, the distal end of the cable flexible tube 204 and the cable 202 are fitted into the hole 193 in the push-button 183 as shown in FIGS. 17 and 18. The remote plunger 206 can be depressed with respect to a plunger stop 208 as shown in FIG. 18 to advance the cable distal end against the stop member 191. The push-button 183 does not move, but the stop member 191 and elongated shaft 186 are moved distally, and the spring 190 is compressed resulting in movement of the movable cutting blade 184 alongside and past the fixed cutting member 174 as shown in FIG. 18.

In use, surgeon can position the fixed cutting blade 174 against the vessel wall and move the fixed cutting blade into the body vessel following the steps illustrated in FIGS. 7A-7D with one hand grasping the elongated tube 172 and the other hand grasping and depress the remote plunger 204 to move the movable cutting blade 184 past the fixed cutting blade 174 as shown in FIG. 18 to cut the slit through the vessel wall pursuant to the step illustrated in FIG. 7E.

Figure 19:
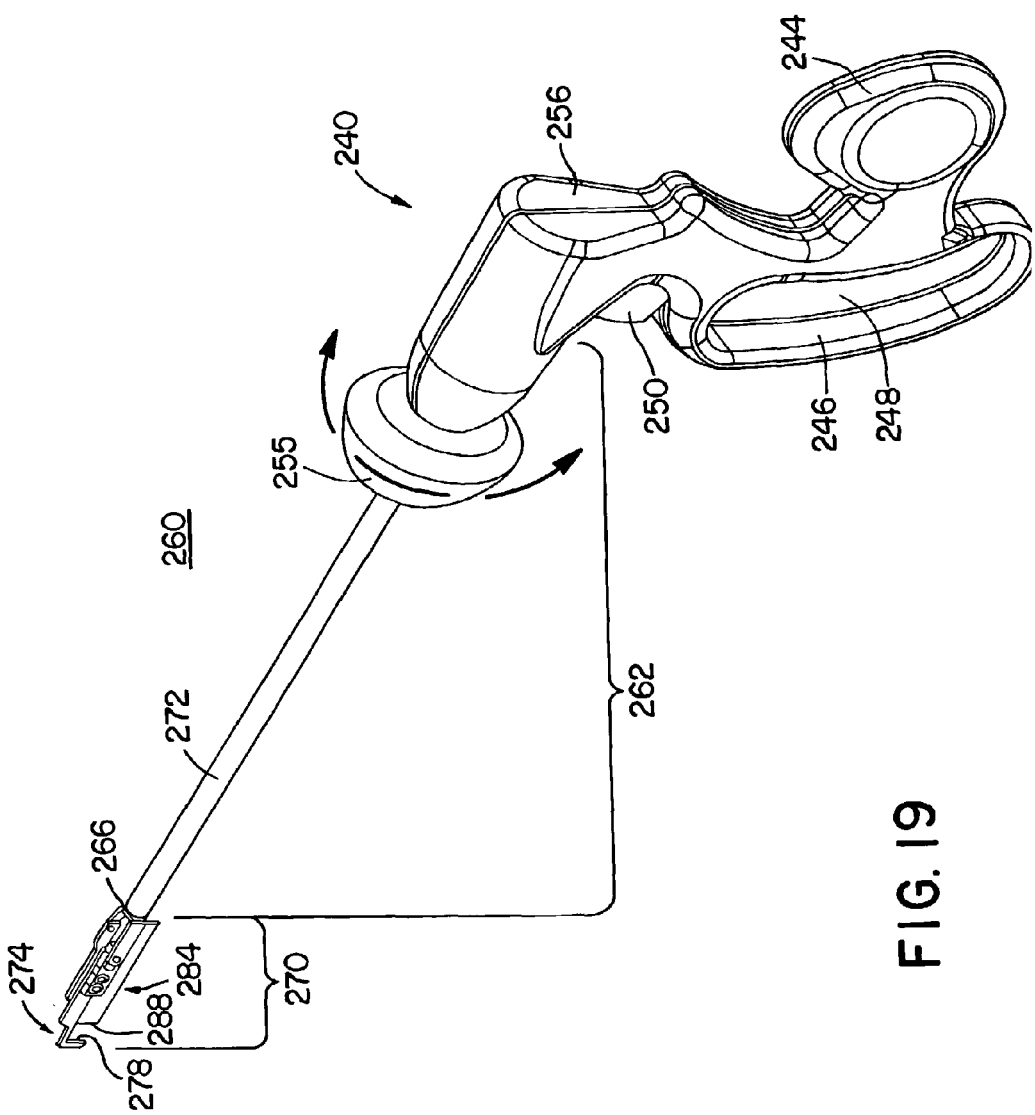
FIG. 19 is a perspective view of a third preferred embodiment of a vessel wall cutting instrument of the present invention with the movable cutting blade in the retracted position.
Figure 20:
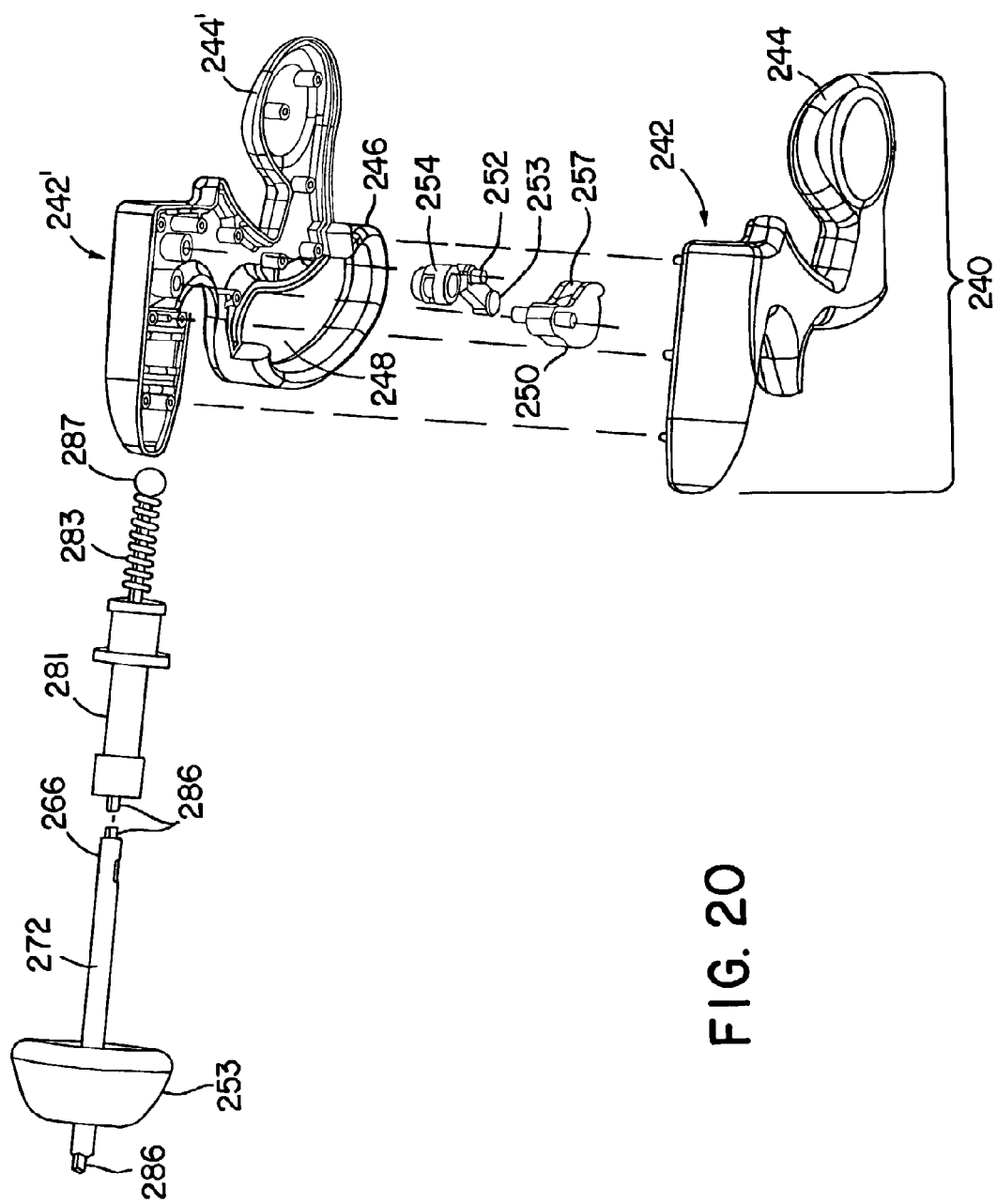
FIG. 20 is a partial exploded perspective view of the proximal portion of the third preferred embodiment of the vessel wall cutting instrument FIG. 19.

A further preferred embodiment of a vessel wall cutting instrument 260 having an elongated shaft 262 extending between shaft proximal and distal ends 264 and 266 is depicted in FIGS. 19-24. A pistol grip handle 240 is depicted in FIGS. 19-21 that the shaft proximal end 264 extends into, and a vessel wall cuffing head 270 is attached to the shaft distal end 266. The elongated shaft 262 and vessel wall cutting head 270 can be rotated with respect to the handle 240 to any desired angular orientation by rotation of shaft rotating collet 255 with respect to pistol grip handle 240. The fixed and movable cutting blades 274 and 284 of vessel wall cutting head 270 are offset at the shaft distal end 266 to the axis of the elongated shaft 262 to make it easier for the user grasping the handle 240 to see the fixed and movable cutting blades 274 and 284 when used in the steps illustrated in FIGS. 7A-7F and when used in conjunction with stabilization illustrated in FIG. 12 and described above. The parts of the vessel wall cutting head 270 in relation to the shaft distal end 266 are shown separated apart in FIG. 24 for convenience of illustration of their configuration and interconnection.

As shown in FIGS. 20 and 21, the handle 240 is formed of left and right handle frame halves 242, 242', and includes a movable trigger 250, and a trigger interlock 252. The movable trigger 250, and a trigger interlock 252 are mounted on pivot points within the left and ring handle frame halves 242, 242'. A socket 254 is formed at one end of the trigger interlock 252, and a lever arm 253 at the other end of the trigger interlock 252 fits into a slot 257 of trigger 250. The pivoting of the movable trigger 250 about its pivot causes the trigger interlock 252 to move about its pivot and to move the socket 254 distally as described below.

Figure 22:
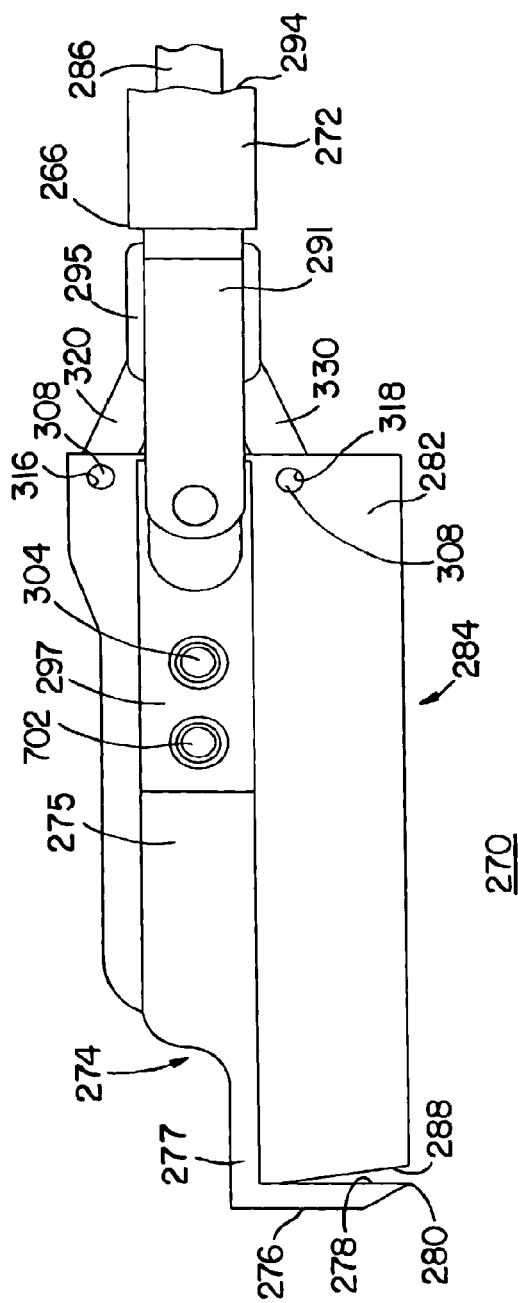
FIG. 22 is a top view of the fixed and movable cutting blades of the cutting head of the vessel wall cutting instrument of FIG. 19.
Figure 23:
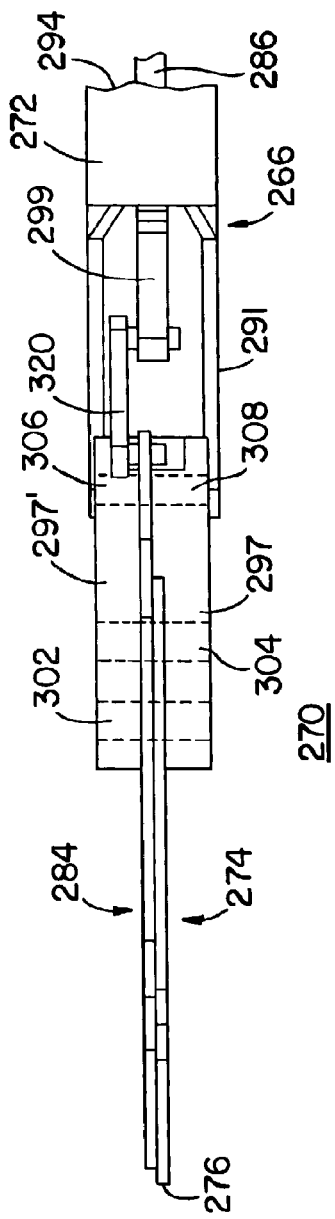
FIG. 23 is a top view of the fixed and movable cutting blades of the cutting head of the vessel wall cutting instrument of FIG. 19.
Figure 24:
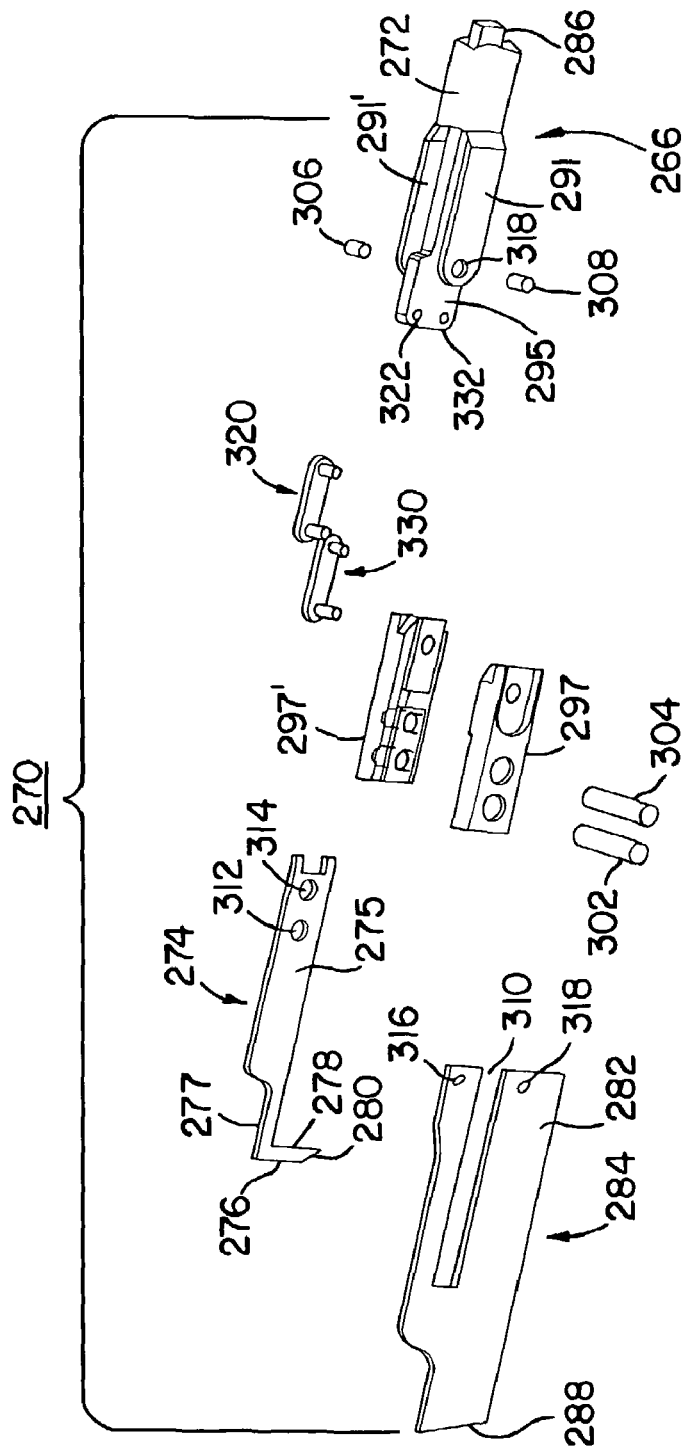
FIG. 24 is an exploded isometric view of the components of the cutting head of the vessel wall cutting instrument of FIG. 19.

An elongated, rectangular cross-section, push-pull bar 286 extends through the length of the lumen 294 of the outer tube 272 of the elongated shaft 262 between a proximal ball 287 shown in FIGS. 20 and 21 and a distal mounting plate 295 shown in FIGS. 22-24. The outer tube 272 functions as a fixed shaft member, and the push-pull bar 286 functions as a movable shaft member. As shown in FIGS. 20 and 21, a coiled wire spring 283 is fitted over the push-pull bar 286 adjacent the proximal ball 287, a shaft mount bearing 281 is fitted over a proximal end portion of the outer tube 272, and the shaft rotating collet 255 is fixedly attached to the outer tube 272 distal to the shaft rotating collet 255. In assembly, the push-pull bar connecting ball 287 is fitted into the trigger interlock socket 254, and the spring 283 and the shaft mount bearing 281 are fitted into a receptacle formed by the left and ring handle frame halves 242, 242' that is shaped to mate with the outer shape of the shaft rotating collet 255 as shown in FIG. 21.

When the trigger 250 is released as shown in FIG. 19, the spring 283 biases or pulls the push-pull bar connecting ball 287 proximally, that is away from the distal vessel wall cutting head 270. The elongated push-pull bar 286 is pulled proximally within lumen 296 causing the cutting edge 288 of the movable cutting blade 284 to be pulled proximally away from the fixed cutting edge 278 of the fixed cutting blade 274 into a retracted position.

When the trigger 250 is pulled as shown in FIG. 21, the trigger lock 252 is pivoted to move socket 254 distally, thereby compressing spring 283 and moving the push-pull bar connecting ball 287 distally into wall cutting head 270. The elongated push-pull bar 286 is pushed distally within lumen 294 causing the cutting edge 288 of the movable cutting blade 284 to be pushed distally toward and alongside the fixed cutting edge 278 of the fixed cutting blade 274.

The handle 240 is shaped with a knob or grip 244 that fits in the surgeon's palm as the index finger is applied to the trigger 250 and the remaining fingers are curled and fit into opening 246 within loop 248. The surgeon's thumb can be applied against the surface 256 to stabilize the grip that is achieved. Loop 248 is shaped to comfortably fit the natural curve of a human user's fingers, and surface 256 provides greater control in movement of the vessel wall cutting instrument 260. The surgeon can grasp the shaft rotating collet 255 with the fingers of the other hand and rotate the collet 255 and attached elongated shaft 262 with respect to the pistol grip handle 240 to rotate the distal vessel wall cutting head to 270 any desired angular orientation. The elongated shaft 262 rotates within the lumen of the shaft mount bearing 281, and the push-pull bar connecting ball 287 rotates within the trigger interlock socket 254 as the collet 255 is rotated.

The vessel wall cutting head 270 is shown in greater detail in FIGS. 22-24. The fixed and movable cutting blades 274 and 284 comprise elongated fixed and movable cutting blade mounting plates 275 and 285, respectively. A pair of mounting holes 312 and 314 extend through the fixed cutting blade mounting plate 275, and a shank 277 extends distally from fixed cutting blade mounting plate 275 to the laterally extending fixed cutting blade 274. The fixed cutting blade 274 is formed with a trailing fixed cutting edge 278 facing proximally, a leading blunt edge or side 276 and a cutting tip 280. The movable cutting blade mounting plate 282 is formed with a leading fixed cutting edge 288, an elongated slot 310, and a pair of mounting holes 316 and 318.

The outer tube 272 is bifurcated at the shaft distal end 266 into first and second mounting forks 291 and 291'. First and second blade mounting blocks 297 and 297' are attached to the first and second mounting forks 291 and 291', respectively, to extend distally therefrom substantially in parallel, by mounting pins 306 and 308. A fixed cutting blade mounting plate 275 is attached to the second mounting plate 297' to extend distally therefrom employing pins 302 and 304 that fit through pairs of holes in the first and second blade mounting blocks 297 and 297' and the holes 312 and 314, respectively, of the fixed cutting blade mounting plate 275. A channel is formed between the first and second blade mounting blocks 297 and 297' that the movable cutting blade mounting plate 282 is fitted into with the pins 302 and 304 within the elongated slot 310.

The movable cutting blade 284 is then attached to the elongated push-pull bar 286 by first and second linking bars 320 and 322. Proximal pins of linking bars 320 and 322 are fitted into upper and lower holes 322 and 332 of the distal mounting plate 295. Distal pins of linking bars 320 and 322 are fitted into upper and lower holes 316 and 318 of the movable cutting blade mounting plate 282. Distal, pushing, and proximal, pulling, movement of the push-pull bar 286 by pulling and releasing, respectively, trigger 250 is transmitted through the linking bars 320 and 322 to the movable cutting blade 284 to move it along the pins 302 and 304. The movable cutting blade 284 is thereby moved between the advanced, cutting position, wherein the fixed and movable cutting edges 288 and 278, respectively, are substantially in side-by-side alignment to shear the vessel wall and form a slit therein, and the retracted positions shown in FIGS. 21 and 19, respectively.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of mechanical instruments that are not disclosed and are not necessary to the practice of the present invention. In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A vessel wall cutting instrument for making an elongated slit through a vessel wall of a body vessel of a patient having a vessel axis from an exterior surface to an interior surface of the vessel wall into a lumen of the body vessel comprising:
   an elongated instrument shaft extending between a shaft proximal end and a shaft distal end and having an instrument shaft axis the elongated instrument shaft comprising a fixed shaft member and a movable shaft member adapted to move with respect to the fixed shaft member in the direction of the instrument shaft axis;
   a fixed cutting blade fixed to the fixed shaft member at the shaft distal end to extend substantially laterally to the instrument shaft axis to a fixed cutting blade free end, the fixed cutting blade having a blunt distal leading blade side, a proximal, trailing side having a fixed cutting edge, and a cutting tip at the fixed cutting blade free end; wherein the fixed cutting edge of the proximal trailing side is generally straight along the direction of the laterally extending fixed cutting blade, and wherein the blunt distal leading blade side includes a major portion spaced-apart from the cutting tip, wherein the major portion extends generally perpendicular to the proximal trailing side;
   a movable cutting blade having a distal, leading edge fixed to the movable shaft member at the shaft distal end, the movable cutting blade extending substantially laterally to the shaft axis and having a movable cutting edge along the movable cutting blade distal, leading edge;
   means for maintaining the movable shaft member in a retracted position with the movable cutting blade spaced proximally from the fixed cutting member as the blunt distal leading blade side is applied against the exterior surface of the vessel wall to depress the vessel wall and is moved laterally to pass the cutting tip of the fixed cutting blade through the vessel wall and into the lumen of the body vessel; and
   means for moving the movable shaft member with respect to the fixed shaft member between the retracted position separating the fixed and movable cutting edges and an extended position wherein the fixed and movable cutting edges are substantially in side-by-side alignment to shear the vessel wall and form a slit therein.

2. The vessel wall cutting instrument of claim 1, wherein:
   the fixed cutting blade is disposed to extend laterally to the shaft axis by a shank having a shank proximal end mounted to the fixed shaft member at the shaft distal end and extending distally substantially in parallel with the instrument shaft axis and alongside the movable cutting blade to a shank distal end; and
   the fixed cutting blade extends laterally to the shaft axis from the shank distal end to the fixed cutting blade free end and has a substantially straight fixed cutting edge, whereby the cutting tip at the fixed cutting blade free end is disposed against a body vessel wall substantially in alignment with the vessel axis as the blunt distal leading blade side is applied against the exterior surface of the vessel wall to depress the vessel wall and is moved laterally to pass the cutting tip of the fixed cutting blade through the vessel wall and into the lumen of the body vessel.

3. The vessel wall cutting instrument of claim 2, wherein:
   the means for maintaining the movable shaft member in a retracted position comprises a spring mounted between the fixed shaft member and the movable shaft member and exerting retraction force therebetween; and
   the moving means comprises means for transmitting force overcoming the retraction force to the movable shaft member to move the movable shaft member with respect to the fixed shaft member between the retracted position and the extended position.

4. The vessel wall cutting instrument of claim 2, further comprising means for applying suction to the body tissue alongside the body vessel to stabilize the body vessel from movement.

5. The vessel wall cutting instrument of claim 2, further comprising means for applying an occlusion frame against the body vessel and body tissue alongside the body vessel to compress the body vessel lumen and inhibit blood loss through the elongated slit.

6. The vessel wall cutting instrument of claim 2, further comprising means for applying compressive force to the body vessel alongside the body vessel to compress and stabilize the body vessel from movement.

7. The vessel wall cutting instrument of claim 1, further comprising means for applying suction to the body tissue alongside the body vessel to stabilize the body vessel from movement.

8. The vessel wall cutting instrument of claim 1, further comprising means for applying an occlusion frame against the body vessel and body tissue alongside the body vessel to compress the body vessel lumen and inhibit blood loss through the elongated slit.

9. The vessel wall cutting instrument of claim 1, further comprising means for applying compressive force to the body vessel alongside the body vessel to compress and stabilize the body vessel from movement.

10. A vessel wall cutting instrument for making an elongated slit through a vessel wall of a body vessel of a patient having a vessel axis from an exterior surface to an interior surface of the vessel wall into a lumen of the body vessel comprising:

an elongated instrument shaft extending between a shaft proximal end and a shaft distal end and having an instrument shaft axis the elongated instrument shaft comprising a first shaft member and a second shaft member adapted to move with respect to one another in the direction of the instrument shaft axis;

a first cutting blade fixed to the first shaft member at the shaft distal end to extend substantially laterally to the instrument shaft axis to a first cutting blade free end, the first cutting blade having a blunt distal leading blade side, a proximal, trailing side having a first cutting edge, and a cutting tip at the first cutting blade free end;

wherein the first cutting edge of the proximal trailing side is generally straight along the direction of the laterally extending first cutting blade, and wherein the blunt distal leading blade side includes a major portion spaced-apart from the cutting tip, wherein the major portion extends generally perpendicular to the proximal trailing side;

a second cutting blade having a distal, leading edge fixed to the second shaft member at the shaft distal end, the second cutting blade extending substantially laterally to the shaft axis and having a second cutting edge along the second cutting blade distal, leading edge;

means for maintaining the first and second shaft members in a retracted position with the second cutting blade spaced proximally from the first cutting blade as the blunt distal leading blade side is applied against the exterior surface of the vessel wall to depress the vessel wall and is moved laterally to pass the cutting tip of the first cutting blade through the vessel wall and into the lumen of the body vessel; and means for moving the first and second shaft members together from the retracted position to bring the first and second cutting edges substantially in side-by-side alignment to shear the vessel wall therebetween and form a slit therein.

11. The vessel wall cutting instrument of claim 10, wherein:

the first cutting blade is disposed to extend laterally to the shaft axis by a shank having a shank proximal end mounted to the first shaft member at the shaft distal end and extending distally substantially in parallel with the instrument shaft axis and alongside the second cutting blade to a shank distal end; and the first cutting blade extends laterally to the shaft axis from the shank distal end to the first cutting blade free end and has a substantially straight first cutting edge, whereby the cutting tip at the first cutting blade free end is disposed against a body vessel wall substantially in alignment with the vessel axis as the blunt distal leading blade side is applied against the exterior surface of the vessel wall to depress the vessel wall and is moved laterally to pass the cutting tip of the first cutting blade through the vessel wall and into the lumen of the body vessel.

12. The vessel wall cutting instrument of claim 11, wherein:

the means for maintaining the first and second shaft members in a retracted position comprises a spring mounted between the first shaft member and the second shaft member and exerting retraction force therebetween; and the moving means comprises means for transmitting force overcoming the retraction force to move the second shaft member with respect to the fixed shaft member between the retracted position and the extended position.

13. The vessel wall cutting instrument of claim 11, further comprising means for applying suction to the body tissue alongside the body vessel to stabilize the body vessel from movement.

14. The vessel wall cutting instrument of claim 11, further comprising means for applying an occlusion frame against the body vessel and body tissue alongside the body vessel to compress the body vessel lumen and inhibit blood loss through the elongated slit.

15. The vessel wall cutting instrument of claim 11, further comprising means for applying compressive force to the body vessel alongside the body vessel to compress and stabilize the body vessel from movement.

16. The vessel wall cutting instrument of claim 10, further comprising means for applying an occlusion frame against the body vessel and body tissue alongside the body vessel to compress the body vessel lumen and inhibit blood loss through the elongated slit.

17. The vessel wall cutting instrument of claim 10, further comprising means for applying compressive force to the body vessel alongside the body vessel to compress and stabilize the body vessel from movement.

* * * * *

UNITED STATES PATENT AND TRADEMARK OFFICE
CERTIFICATE OF CORRECTION

PATENT NO. : 8,377,082 B2
APPLICATION NO. : 10/694037
DATED : February 19, 2013
INVENTOR(S) : Clague et al.

It is certified that error appears in the above-identified patent and that said Letters Patent is hereby corrected as shown below:

In the Claims:

Column 21, line 41, Claim 1

"an elongated instrument shaft extending between a shaft proximal end and a shaft distal end and having an instrument shaft axis the elongated instrument shaft comprising a fixed shaft member and a movable shaft member adapted to move with respect to the fixed shaft member in the direction of the instrument shaft axis;"

should be changed to

--an elongated instrument shaft extending between a shaft proximal end and a shaft distal end and having an instrument shaft axis, the elongated instrument shaft comprising a fixed shaft member and a movable shaft member adapted to move with respect to the fixed shaft member in the direction of the instrument shaft axis;--

Signed and Sealed this
Sixteenth Day of July, 2013

Teresa Stanek Rea
*Acting Director of the United States Patent and Trademark Office*